US010052139B2

(12) United States Patent
Bucci et al.

(10) Patent No.: US 10,052,139 B2
(45) Date of Patent: Aug. 21, 2018

(54) FLEXIBLE AND STATIC INTERSPINOUS/INTER-LAMINAR SPINAL SPACERS

(71) Applicant: Life Spine, Inc., Huntley, IL (US)

(72) Inventors: Kara A. Bucci, Chicago, IL (US); Madeline Wolters, Carol Stream, IL (US); Michael S. Butler, St. Charles, IL (US)

(73) Assignee: Life Spine, Inc., Huntley, IL (US)

( * ) Notice: Subject to any disclaimer, the term of this patent is extended or adjusted under 35 U.S.C. 154(b) by 0 days.

(21) Appl. No.: 15/243,389

(22) Filed: Aug. 22, 2016

(65) Prior Publication Data

US 2016/0354124 A1 Dec. 8, 2016

Related U.S. Application Data

(63) Continuation-in-part of application No. 14/281,619, filed on May 19, 2014, now Pat. No. 9,421,043, which is a continuation of application No. 13/567,581, filed on Aug. 6, 2012, now Pat. No. 8,728,123, which is a continuation of application No. 12/694,051, filed on Jan. 26, 2010, now Pat. No. 8,236,031.

(Continued)

(51) Int. Cl.
*A61B 17/70* (2006.01)
*A61B 17/56* (2006.01)

(52) U.S. Cl.
CPC ...... *A61B 17/7068* (2013.01); *A61B 17/7062* (2013.01); *A61B 2017/564* (2013.01)

(58) Field of Classification Search
CPC ............ A61B 17/7062; A61B 17/7067; A61B 17/7068

USPC ...................... 606/246–249; 623/17.11–17.16
See application file for complete search history.

(56) References Cited

U.S. PATENT DOCUMENTS 4,466,426 A 8/1984 Blackman
4,636,217 A 1/1987 Ogilvie et al.
(Continued)

FOREIGN PATENT DOCUMENTS

WO WO-2006/102485 9/2006

OTHER PUBLICATIONS

"Bacfuse® Spinous Process Fusion Plate Surgical Technique", © 2011, Pioneer Surgical, 12 pages.

*Primary Examiner* — Ellen C Hammond
*Assistant Examiner* — Christina Negrellirodrigue
(74) *Attorney, Agent, or Firm* — Foley & Lardner LLP

(57) ABSTRACT

Interspinous/inter-laminar spinal spacers are configured to be placed between bony structures of adjacent vertebrae. In one form, a spinal spacer includes a body including a first plate having a first wing configured to engage a first vertebra and a second wing configured to engage a second vertebra, and a post extending from the first plate to define a longitudinal axis, the post having a bullet nose; a second plate slidably coupled to the post of the body, the second plate including a first wing configured to engage the first vertebra; and a second wing configured to engage the second vertebra; wherein the second plate defines a first bore configured to receive the post, and wherein the bullet nose is designed to pierce through an interspinous ligament between the first vertebra and the second the vertebra so that the interspinous ligament can hold the implant in place.

16 Claims, 14 Drawing Sheets

Related U.S. Application Data

(60) Provisional application No. 61/147,384, filed on Jan. 26, 2009.

(56) References Cited

U.S. PATENT DOCUMENTS

| | | | |
|---|---|---|---|
| 5,645,599 A | 7/1997 | Samani | |
| 5,836,948 A | 11/1998 | Zucherman et al. | |
| 5,860,977 A | 1/1999 | Zucherman et al. | |
| 5,876,404 A | 3/1999 | Zucherman et al. | |
| 6,048,342 A | 4/2000 | Zucherman et al. | |
| 6,068,630 A | 5/2000 | Zucherman et al. | |
| 6,074,390 A | 6/2000 | Zucherman et al. | |
| 6,183,471 B1 | 2/2001 | Zucherman et al. | |
| 6,190,387 B1 | 2/2001 | Zucherman et al. | |
| 6,235,030 B1 | 5/2001 | Zucherman et al. | |
| 6,451,019 B1 | 9/2002 | Zucherman et al. | |
| 6,695,842 B2 | 2/2004 | Zucherman et al. | |
| 6,699,246 B2 | 3/2004 | Zucherman et al. | |
| 6,699,247 B2 | 3/2004 | Zucherman et al. | |
| 6,743,257 B2 | 6/2004 | Castro | |
| 6,796,983 B1 | 9/2004 | Zucherman et al. | |
| 7,101,375 B2 | 9/2006 | Zucherman et al. | |
| 7,695,513 B2 | 4/2010 | Zucherman et al. | |
| 8,231,656 B2 * | 7/2012 | Lee | A61B 17/7068 606/249 |
| 8,603,142 B2 * | 12/2013 | Robinson | A61B 17/7068 606/249 |
| 2003/0236520 A1 | 12/2003 | Lim et al. | |
| 2005/0222681 A1 | 10/2005 | Richley et al. | |
| 2005/0261768 A1 | 11/2005 | Trieu | |
| 2005/0261769 A1 | 11/2005 | Moskowitz et al. | |
| 2005/0278036 A1 | 12/2005 | Leonard et al. | |
| 2006/0036258 A1 | 2/2006 | Zucherman et al. | |
| 2006/0084988 A1 | 4/2006 | Kim | |
| 2006/0089718 A1 | 4/2006 | Zucherman et al. | |
| 2006/0241601 A1 | 10/2006 | Trautwein et al. | |
| 2006/0264938 A1 | 11/2006 | Zucherman et al. | |
| 2006/0293662 A1 | 12/2006 | Boyer et al. | |
| 2007/0142915 A1 | 6/2007 | Altarac et al. | |
| 2007/0173823 A1 | 7/2007 | Dewey et al. | |
| 2008/0114456 A1 | 5/2008 | Dewey et al. | |
| 2008/0161818 A1 | 7/2008 | Kloss et al. | |
| 2008/0177391 A1 * | 7/2008 | Mitchell | A61B 17/7065 623/17.16 |
| 2008/0183211 A1 | 7/2008 | Lamborne et al. | |
| 2008/0312741 A1 | 12/2008 | Lee et al. | |
| 2009/0270919 A1 | 10/2009 | Dos Reis, Jr. | |
| 2010/0004688 A1 | 1/2010 | Maas et al. | |
| 2010/0036419 A1 | 2/2010 | Patel et al. | |
| 2010/0204732 A1 | 8/2010 | Aschmann et al. | |
| 2010/0241167 A1 | 9/2010 | Taber et al. | |
| 2011/0022090 A1 | 1/2011 | Gordon et al. | |
| 2011/0066186 A1 | 3/2011 | Boyer et al. | |
| 2011/0144692 A1 | 6/2011 | Saladin et al. | |
| 2011/0172709 A1 | 7/2011 | Lyons et al. | |
| 2011/0184468 A1 | 7/2011 | Metcalf et al. | |

* cited by examiner

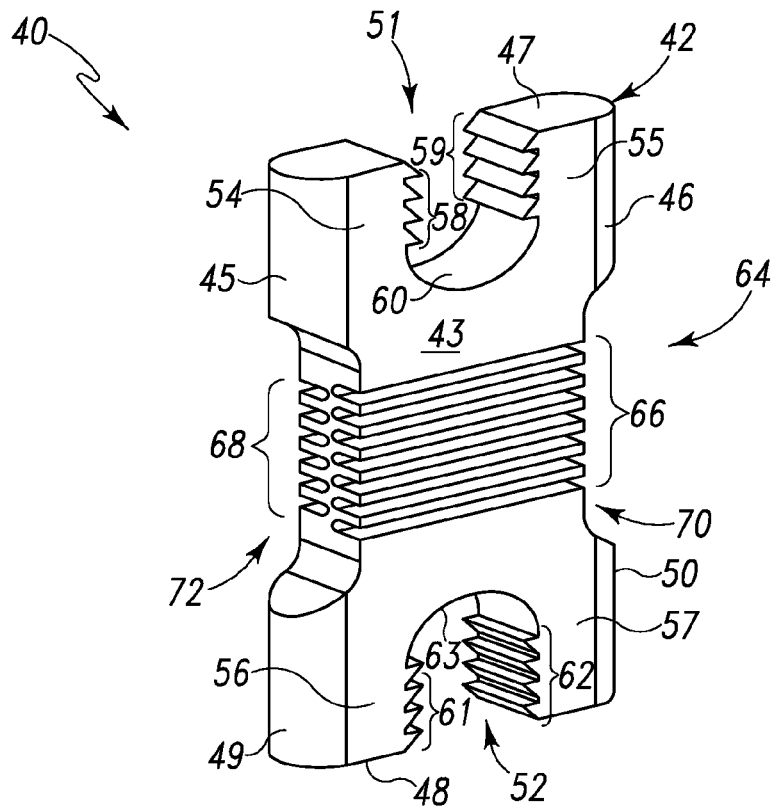
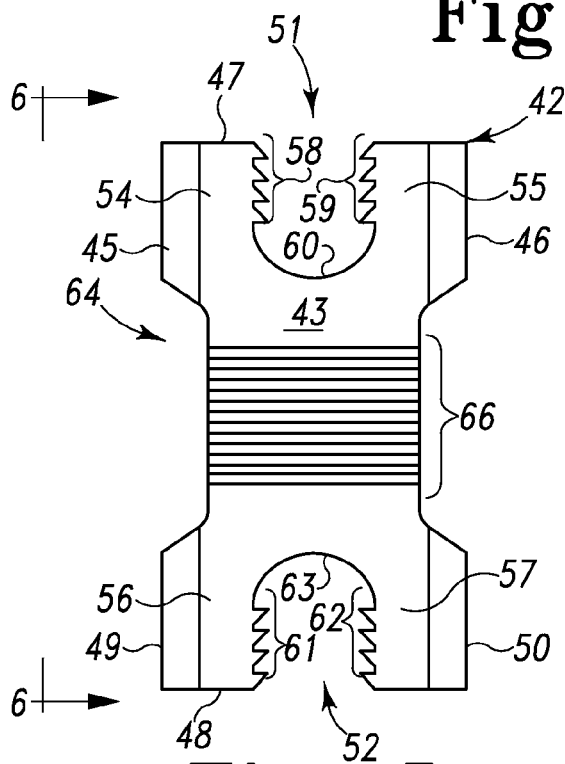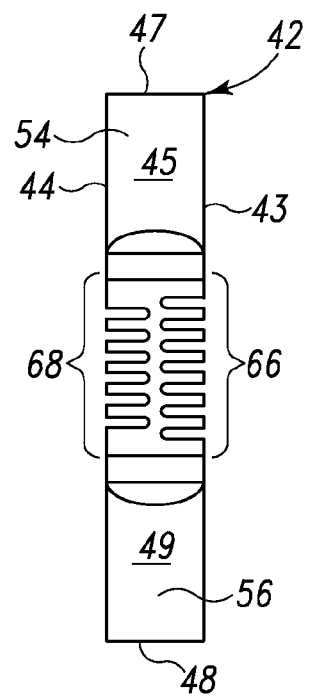
Fig. 4
Fig. 5  Fig. 6

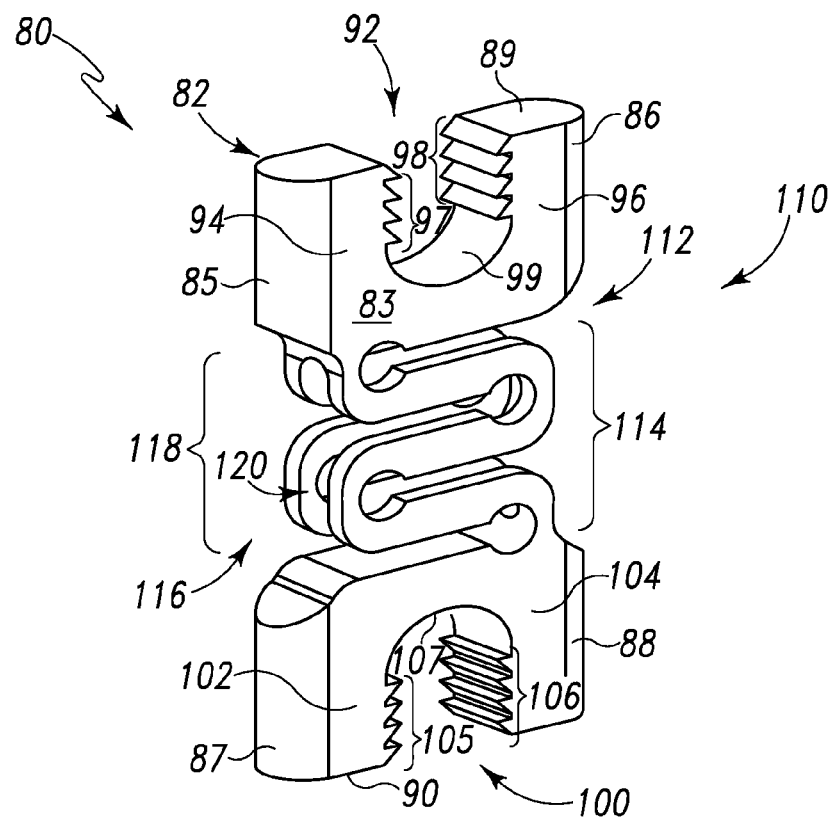
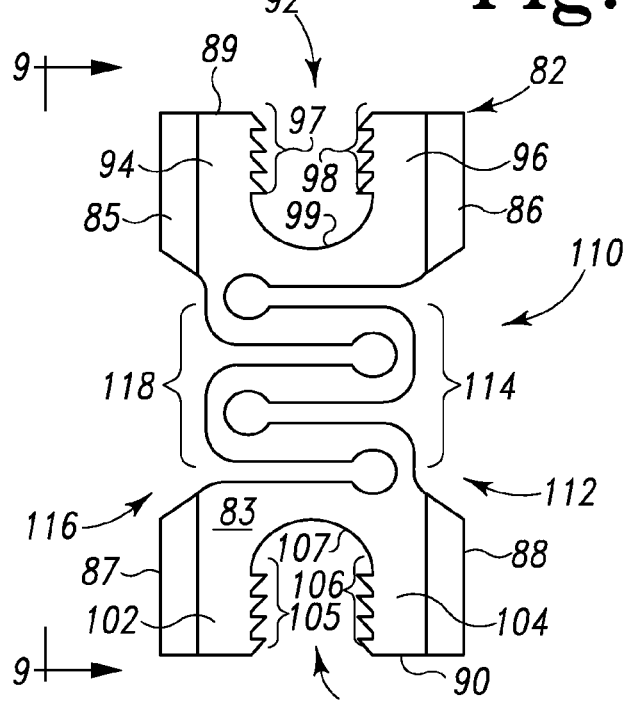 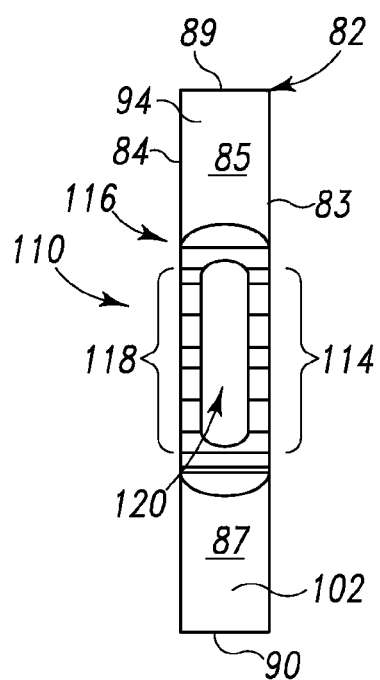
Fig. 7
Fig. 8  Fig. 9

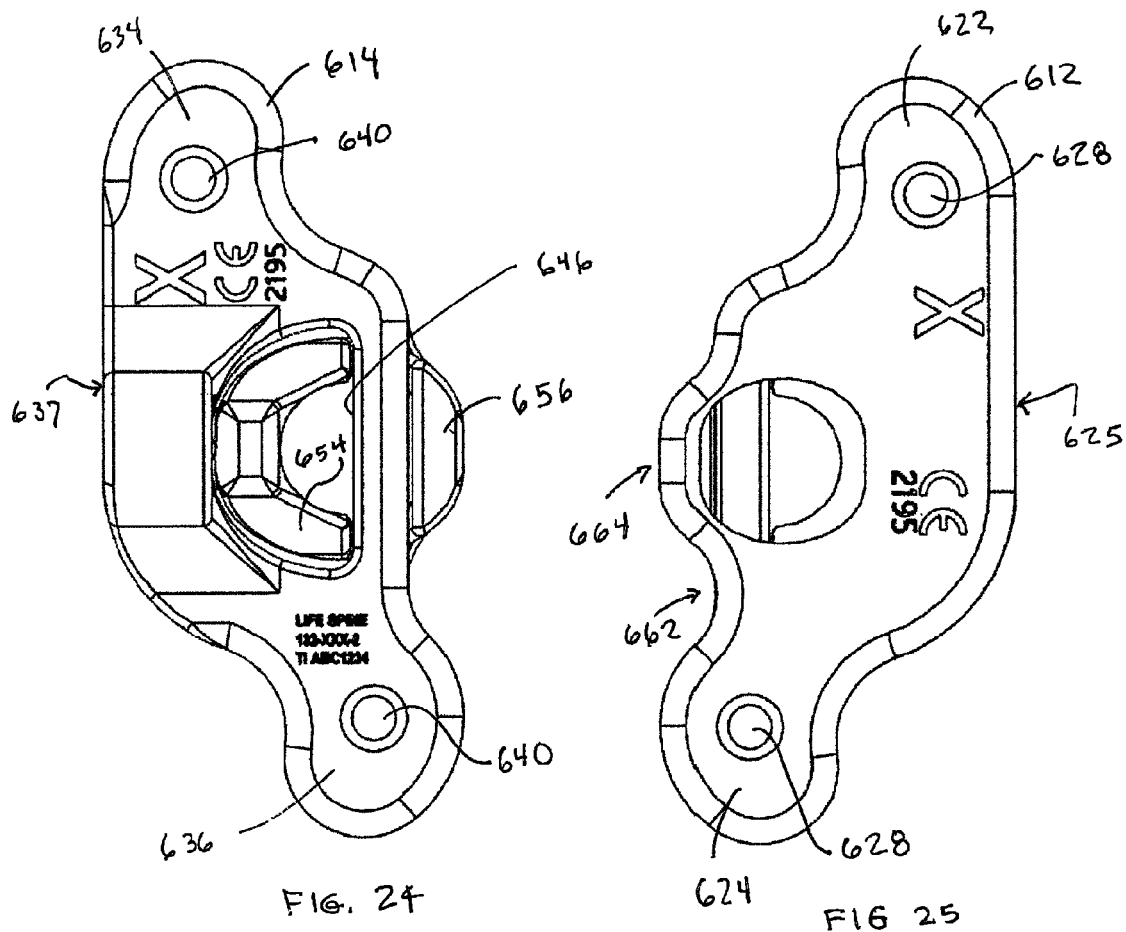
FIG. 24
FIG. 25
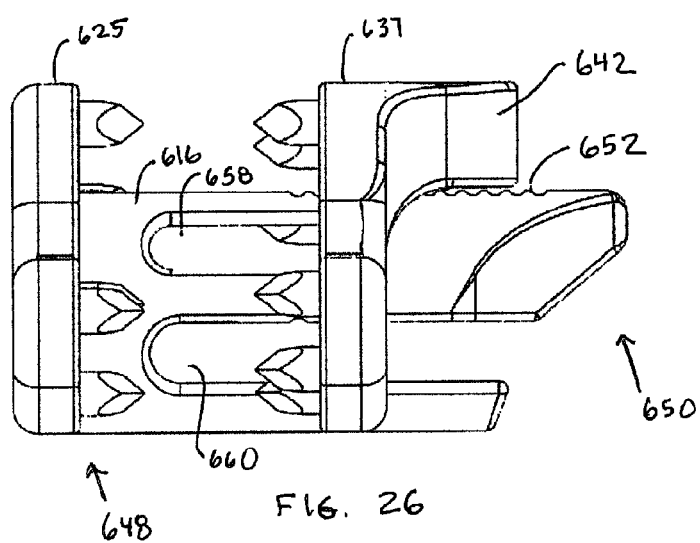
FIG. 26

FLEXIBLE AND STATIC INTERSPINOUS/INTER-LAMINAR SPINAL SPACERS

CROSS-REFERENCE TO RELATED PATENT APPLICATIONS

This application is a continuation-in-part of application Ser. No. 14/281,619, filed May 19, 2014, which is a continuation of application Ser. No. 13/567,581, filed Aug. 6, 2012, now U.S. Pat. No. 8,728,123, which is a continuation of application Ser. No. 12/694,051 filed Jan. 26, 2010, now U.S. Pat. No. 8,236,031, which claims the benefit of Provisional Application No. 61/147,384, filed Jan. 26, 2009. The entire contents of all of these applications are incorporated herein by reference.

BACKGROUND

The present disclosure relates to devices for the spine and, more particularly, to spinal implants for providing interspinous and/or inter-laminar space between adjacent vertebrae.

As we age various changes can occur in the body. For instance, the ligaments of the spine can thicken and calcify (i.e. harden from deposits of calcium), bone and joints may enlarge, bone spurs called osteophytes may form, spinal discs may collapse and bulge (i.e. herniate) or one vertebra may slip over another (spondylolisthesis). Any one or these conditions and/or others can cause what is known as lumbar spinal stenosis. Lumbar spinal stenosis is a narrowing of the bony spinal canal. While some people are born with this condition, most often spinal stenosis is the result of one of the above-identified degenerative conditions that develop in mainly the middle-aged and elderly population.

In this regard, spinal stenosis may be considered as the gradual result of aging and "wear and tear" on the spine from everyday activities. Such degenerative or age-related changes in our bodies can lead to compression of nerves (i.e. pressure on the nerves that can cause pain and/or damage). Symptoms of lumbar spinal stenosis include leg pain ("pins and needles") that can limit standing, walking, self-supporting daily activities, work social and recreational pursuits. Lack of activity because of lumbar spinal stenosis may lead to obesity, depression and general physical deterioration. Surgical procedures may be used in order to alleviate the problems associated with spinal stenosis. This may include the use of an implant designed to hold or stabilize adjacent vertebrae or vertebral parts of the spine.

Other spinal conditions, diseases and/or accidents, however, can also cause problems that may require spinal surgery and the need to hold or stabilize adjacent vertebrae or vertebral parts in a spatial orientation relative to one another and/or with regard to other vertebral parts. In these cases, the surgeon may again use a device to hold or stabilize adjacent vertebrae or vertebral parts. The implants used for these purposes are typically not affixed to the vertebrae by bone screws or the like but are held to the vertebrae by the bony portions, structures or protrusions of the vertebrae.

Of these types of spinal devices some allow for movement between the adjacent vertebrae to which it is connected and some do not. The static spinal device provides a fixed or static spatial orientation of the adjacent vertebrae to which it is affixed. The static spinal devices permanently limit movement between the adjacent vertebrae to which it is affixed. The non-static spinal devices provide limited movement between the adjacent vertebrae in addition to maintaining a spatial orientation of the adjacent vertebrae. These non-static spinal devices, however, are assemblies formed of two or more components with a variety of ways to achieve motion between the various components.

In view of the above, it is apparent that there is a need for improved interspinous or inter-laminar spinal devices, both flexible and static one-piece designs.

SUMMARY

The inventive concepts disclosed herein provide interspinous/inter-laminar spinal spacers (processes, transverse and spinous—i.e. spinal spacers) that are configured to be placed between bony structures of adjacent vertebrae of a spine.

In one form, a flexible interspinous/inter-laminar spinal spacer (processes, transverse and spinous—i.e. flexible spinal spacer) is defined by a unitary body that is configured to be placed between bony structures of adjacent vertebrae of a spine. The unitary body has a flex portion that provides for motion between the adjacent vertebrae to which it is coupled. The flex portion is configurable to provide for various degrees of angulation, flexion, extension and/or compression of the present flexible spinal spacer. Thus, the present flexible spinal spacer allows for controlled movement of the adjacent vertebrae to which it is attached, as well as aid in insertion and/or implantation of the flexible spinal spacer.

The flex portion may take different configurations depending on the type, degree and/or amount of flexure. In one form, the flex portion comprises a plurality of cuts, slits, grooves, channels, notches or the like (collectively, cuts) extending from lateral sides of the unitary body that may or may not be through. The cuts are staggered relative to opposite serrations and may or may not extend diagonally from and along the lateral sides. The size of the cuts, the degree of slant or no slant of the cuts all provides various flexure properties. This allows for various degrees of lateral compression of the flexible spinal spacer. Other configurations are thus contemplated that provide for lateral compression and/or extension of the flexible spinal spacer.

In another form, the flex portion comprises a plurality of posterior and anterior ribs, ledges, shelves, fins, projections or the like (collectively, ribs) extending from a middle section of the unitary body. The ribs are staggered relative to opposite ribs and extend generally perpendicular to the middle section (i.e. in the posterior and anterior direction). The number and size of the anterior/posterior ribs all provide various flexure properties. This allows for various degrees of extension and/or flexion of the flexible spinal spacer. Other configurations are thus contemplated that provide for flexion and/or extension of the flexible spinal spacer.

In another form, the flex portion comprises posterior and anterior flexure contours (e.g. springs or spring-like contours) defined by the posterior and anterior sides of the unitary body. The posterior and anterior flexure contours extend generally from and between the superior end and the inferior end of the unitary body. Each flexure contour comprises one or more curvatures. The number, size, thickness and configuration of the curvatures all provide various flexure properties. A cavity is thus formed between the posterior flexure contour and the anterior flexure contours of the unitary body. This allows for various degrees of angulation, compression, flexion and/or extension of the flexible spinal spacer. Other configurations are thus contemplated that provide for angulation only or angulation, compression, flexion and/or extension of the flexible spinal spacer.

The unitary body of the flexible spinal spacers has saddle-shaped ends each defining a pocket that is configured to receive a bony structure of a vertebra. The pockets may or may not be textured and/or may or may not include teeth, serrations or ridged surfaces to secure the spinal spacer to the bony structure.

The present flexible spinal spacers allow for controlled movement of the adjacent vertebrae to which it is attached, as well as aid in insertion and/or implantation of the flexible spinal spacer.

In another form, static interspinous/inter-laminar spinal spacers (processes, transverse and spinous—i.e. static spinal spacers) are defined by a unitary body that is configured to be placed between bony structures of adjacent vertebrae of a spine. The unitary body has saddle-shaped ends each defining a pocket that is configured to receive a bony structure of a vertebra. The pockets may or may not be textured and/or may or may not include teeth, serrations or ridged surfaces to secure the spinal spacer to the bony structure.

The present spinal spacers are made from a biocompatible material such as PEEK (PolyEtherEtherKetone), titanium, stainless steel or the like that will provide flexure given the geometry or configuration of the unitary body thereof.

Some embodiments relate to a spinal spacer for insertion into a spinal space between a first vertebra and a second vertebra. The spinal spacer includes a body comprising a first plate having a first wing configured to engage the first vertebra and a second wing configured to engage the second vertebra and a post extending from the first plate to define a longitudinal axis, the post having a bullet nose; a second plate slidably coupled to the post of the body, the second plate comprising a first wing configured to engage the first vertebra; and a second wing configured to engage the second vertebra; wherein the second plate defines a first bore configured to receive the post, and wherein the bullet nose is designed to pierce through an interspinous ligament between the first vertebra and the second the vertebra so that the interspinous ligament can hold the implant in place.

Further embodiments relate to a method of implanting a spinal spacer through an interspinous ligament and into a spinal space between a first vertebra and a second vertebra, the method including providing a first plate, a post, and a second plate, the first plate having a first wing and a second wing, the post extending from the first plate to define a longitudinal axis, the post having a bullet nose, the second plate slidably coupled to the post and having a first wing, a second wing, and a bore to receive the post; pushing the bullet nose through the interspinous ligament; inserting the post in the spinal space between the first vertebra and the second vertebra; and inserting the second contoured plate onto the post.

Further embodiments relate to a spinal spacer for insertion into a spinal space between a first vertebra and a second vertebra, the spinal spacer including a body comprising a first plate having a first wing configured to engage the first vertebra and a second wing configured to engage the second vertebra; a post extending from the first plate along a longitudinal axis, the post having a bullet nose configured to pierce through an interspinous ligament between the first vertebra and the second the vertebra; a second plate slidably received on the post, the second contoured plate comprising a first wing configured to engage the first vertebra; a second wing configured to engage the second vertebra; a boss having a threaded first bore with an axis perpendicular to the longitudinal axis of the post; wherein the second plate defines a recess configured to receive the post, wherein positioning of the post within the recess inhibits rotation of the second plate relative to the first plate; a screw received in the threaded first bore in the boss and engaged with the post to secure the second plate relative to the first plate.

BRIEF DESCRIPTION OF THE DRAWINGS

The above mentioned and other features, advantages and objects of this disclosure, and the manner of attaining them, will become apparent and the inventive concepts will be better understood by reference to the following description of embodiments of the invention taken in conjunction with the accompanying drawings, wherein:

FIG. 4 is an isometric view of another embodiment of a flexible interspinous/inter-laminar spinal spacer (processes, transverse & spinous—i.e. flexible spinal spacer);

FIG. 5 is a front view of the flexible spinal spacer of FIG. 4;

FIG. 6 is a side view of the flexible spinal spacer of FIG. 4 taken along line 6-6 of FIG. 5;

FIG. 7 is an isometric view of another embodiment of a flexible interspinous/inter-laminar spinal spacer (processes, transverse & spinous—i.e. flexible spinal spacer);

FIG. 8 is a front view of the flexible spinal spacer of FIG. 7;

FIG. 9 is a side view of the flexible spinal spacer of FIG. 7 taken along line 9-9 of FIG. 8;

FIGS. 24 and 25 are side views of the implant of FIG. 22 according to one embodiment;

FIG. 26 is a top view of the implant of FIG. 22 according to one embodiment;

Like reference numerals indicate the same or similar parts throughout the several figures.

A discussion of the features, functions and/or configurations of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION

Figure 1:
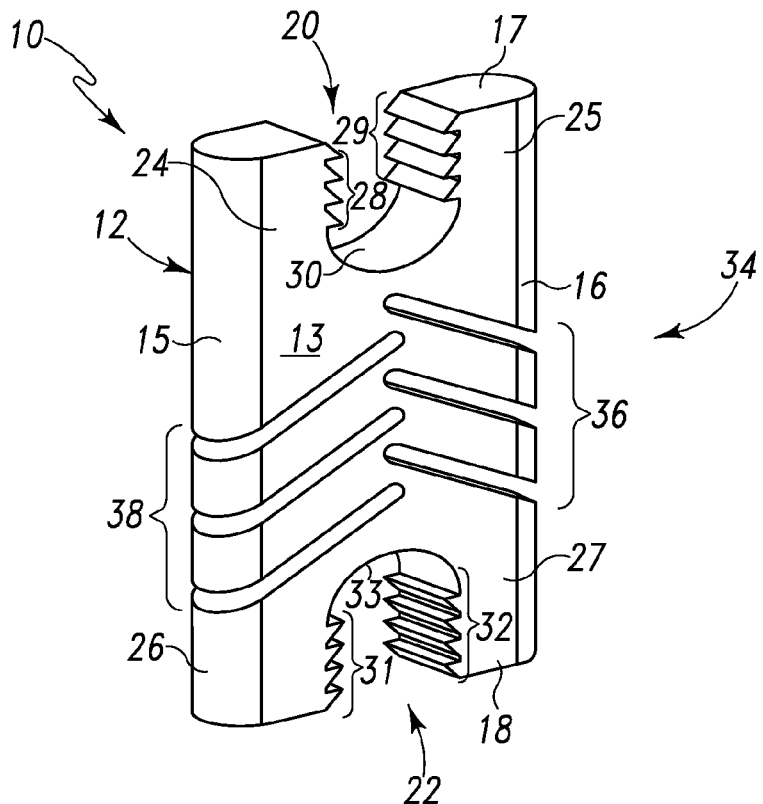
FIG. 1 is an isometric view of an embodiment of a flexible interspinous/inter-laminar spinal spacer (processes, transverse & spinous—i.e. flexible spinal spacer)
Figure 2:
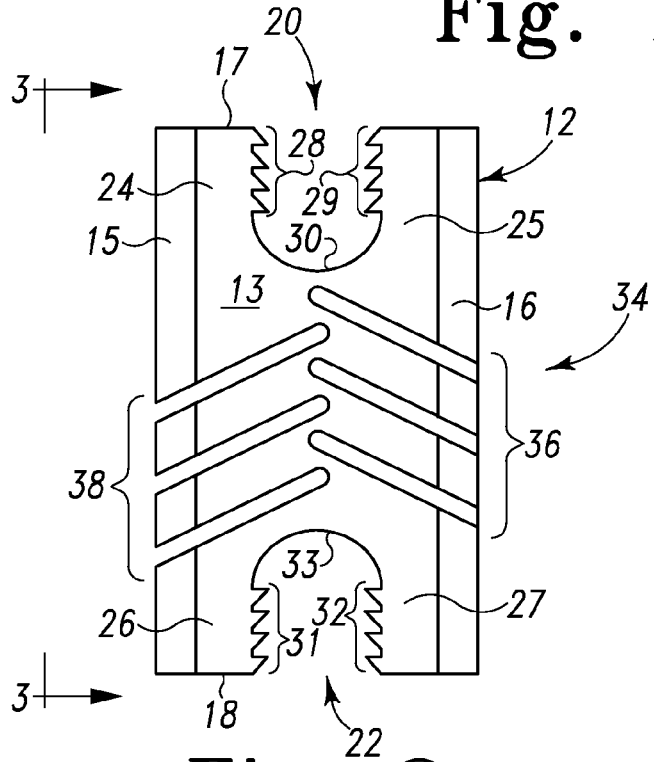
FIG. 2 is a front view of the flexible spinal spacer of FIG. 1.
Figure 3:
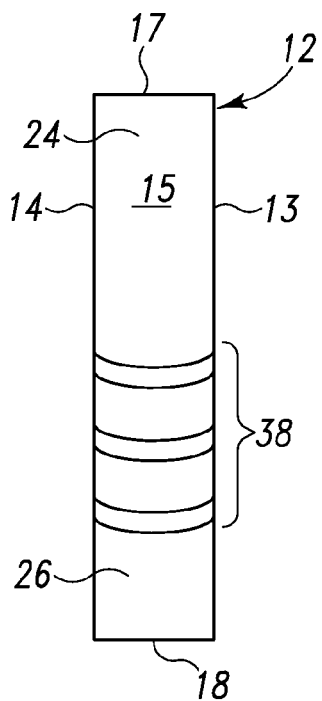
FIG. 3 is a side view of the flexible spinal spacer of FIG. 1 taken along line 3-3 of FIG. 2.

Referring to FIGS. 1-3, there is shown an embodiment of a flexible interspinous or inter-laminar spinal spacer (processes, transverse and spinous—i.e. flexible spinal spacer) generally designated 10 fashioned in accordance with the principles of the present invention. The flexible spinal spacer 10 is used as an interspinous, inter-laminar, interbody, or interbony spinal spacer and thus is configured to be placed between bony structures of adjacent vertebrae of a spine.

The flexible spinal spacer 10 is formed as a unitary or single-piece body 12 of a biocompatible material. The body 12 is formed in a generally "H" shape and thus defines a first lateral side 15, a second lateral side 16, a posterior side 13, an anterior side 14, a superior side or end 17, and an inferior side or end 18. It should be appreciated that the flexible spinal spacer may take forms other than an "H" while maintaining the features and/or characteristics of the present invention. The body 12 also has a flex portion 34 disposed between the superior side 17 and the inferior side 18. The flex portion 34 has flexure characteristics/properties that provide for relative movement or motion of the spinal spacer 10 and thus motion or movement between the adjacent vertebrae to which it is connected. The flex portion 34 is configurable to provide for various degrees of angulation and/or compression of the body 12.

The flex portion 34 comprises a first set, number, or plurality of cuts, slits, grooves, channels, notches or the like 36 (collectively, cuts 36) and a second set, number, or plurality of cuts, slits, grooves, channels, notches or the like 38 (collectively, cuts 38) in the posterior and anterior sides 13, 14 of the body 12. In FIGS. 1-3, the first and second plurality of cuts 36, 38 extend diagonally into the body 12 from the lateral sides 15 and 16 thereof. It should be appreciated that the cuts 36, 38 may be horizontal cuts, perpendicular cuts and/or a pattern of cuts to achieve angulation, flexion, extension and/or compression of the body 12. Also, while three (3) cuts are shown for both the first and second set of cuts 36, 38, it should be appreciated that the number of cuts may vary depending on the desired amount and/or type of flexure.

The superior end 17 is formed as a saddle-shape defining first and second legs 24, 25 separated by a pocket 20 that is configured to receive a bony structure of a superior situated vertebra. The first and second legs 24 and 25 define first and second lateral sides of the pocket 20 with a curved bottom 30. The first lateral side of the pocket 20 has a first plurality of teeth, serrations or ridged surfaces 28 (collectively, teeth) along its length. The first plurality of teeth 28 provide for connection to a first portion of a bony vertebral structure. The second lateral side of the pocket 20 has a second plurality of teeth, serrations or ridged surfaces 29 (collectively, teeth) along its length. The second plurality of teeth 29 provide for connection to a second portion of the bony structure of the superior situated vertebra. The sides of the pocket 20 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony structure of the superior situated vertebra.

The inferior end 18 is formed as a saddle-shape defining third and fourth legs 26, 27 separated by a pocket 22 that is configured to receive a bony structure of an inferior situated vertebra (adjacent to the superior situated vertebra). The third and fourth legs 26 and 27 define first and second lateral sides of the pocket 22 with a curved bottom 33. The first lateral side of the pocket 22 has a first plurality of teeth, serrations or ridged surfaces 31 (collectively, teeth) along its length. The first plurality of teeth 31 provide for connection to a first portion of a bony structure of the inferior vertebra. The second lateral side of the pocket 22 has a second plurality of teeth, serrations or ridged surfaces 32 (collectively, teeth) along its length. The second plurality of teeth 32 provide for connection to a second portion of the bony structure of the inferior situated vertebra. The sides of the pocket 22 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony vertebral structure.

The flexible spinal spacer 10 is thus configured to provide for various degrees of angulation, flexion, extension and/or compression. Thus, the present flexible spinal spacer allows for controlled movement of the adjacent vertebrae to which it is attached (the superior and inferior situated vertebra), as well as aid in insertion and/or implantation of the flexible spinal spacer.

Referring to FIGS. 4-6, there is shown another embodiment of a flexible interspinous or inter-laminar spinal spacer (processes, transverse and spinous—i.e. flexible spinal spacer) generally designated 40 fashioned in accordance with the principles of the present invention. The flexible spinal spacer 40 is used as an interspinous, inter-laminar, interbody, or interbony spinal spacer and thus is configured to be placed between bony structures of adjacent vertebrae of a spine.

The flexible spinal spacer 40 is formed as a unitary or single-piece body 42 of a biocompatible material. The body 42 is formed in a generally "H" shape and thus defines a first superior lateral side 45, a second superior lateral side 46, a first inferior lateral side 49, a second inferior lateral side 50, a posterior side 43, an anterior side 44, a superior side or end 47, and an inferior side or end 48. It should be appreciated that the flexible spinal spacer may take forms other than an "H" while maintaining the features and/or characteristics of the present invention. The body 42 also has a flex portion 64 disposed between the superior side 47 and the inferior side 48. The flex portion 64 has flexure characteristics/properties that provide for relative movement or motion of the spinal spacer 40 and thus motion or movement between the adjacent vertebrae to which it is connected. The flex portion 64 is configurable to provide for various degrees of angulation and/or compression of the body 42.

The flex portion 64 includes a first set, number, or plurality of ribs, ledges, shelves, fins, projections or the like 66 (collectively, ribs 66) [conversely, and/or additionally, a plurality of grooves, slits, channels or the like 66 (collectively, grooves 66) on the posterior side 43 of the body 42 and extending outwardly from a middle portion or section thereof (i.e. extending in the posterior direction). The flex portion 64 further includes a second set, number, or plurality of ribs, ledges, shelves, fins, projections or the like 68 (collectively, ribs 68) [conversely, and/or additionally, a plurality of grooves, slits, channels or the like 68 (collectively, grooves 68) on the anterior side 44 of the body 42 and extending outwardly from the middle portion or section thereof (i.e. extending in the anterior direction). This provides for various flexure properties.

In FIGS. 4-6, the first and second plurality of ribs/grooves 66, 68 extend perpendicular relative to the posterior/anterior faces of the body 42. It should be appreciated that the location and/or shape of the ribs/grooves 66, 68 may be fashioned differently if desired to achieve angulation, flexion, extension and/or compression of the body 42. Also, the number of ribs/grooves and their configuration may vary depending on the desired amount and/or type of flexure and/or flexure properties. Additionally, a first cutout, cavity or depression 72 is defined between the lateral sides 46 and 50 at the junction of the ribs/grooves 66 and ribs/grooves 68 (flex portion 64), while a second cutout, cavity or depression 70 is defined between the lateral sides 45 and 49 at the junction of the ribs/grooves 66 and ribs/grooves 68 (flex portion 64). It should be appreciated that the shape of the cutouts 70, 72 may be fashioned differently than shown to achieve a desired amount and/or type of flexure and/or flexure properties (angulation, flexion, extension and/or compression) of the body 42.

The superior end 47 is formed as a saddle-shape defining first and second legs 54, 55, with leg 54 having the first superior lateral side 45 and leg 55 having the second superior lateral side 46, the legs 54, 55 separated by a pocket 51 that is configured to receive a bony structure of a superior situated vertebra. The first and second legs 54 and 55 define first and second lateral sides of the pocket 51 with a curved bottom 60. The first lateral side of the pocket 51 has a first plurality of teeth, serrations or ridged surfaces 58 (collectively, teeth) along its length. The first plurality of teeth 58 provide for connection to a first portion of a bony vertebral structure. The second lateral side of the pocket 51 has a second plurality of teeth, serrations or ridged surfaces 59 (collectively, teeth) along its length. The second plurality of teeth 59 provide for connection to a second portion of the bony structure of the superior situated vertebra. The sides of the pocket 51 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony structure of the superior situated vertebra.

The inferior end 48 is formed as a saddle-shape defining third and fourth legs 56, 57, with leg 56 having the first inferior lateral side 49 and leg 57 having the second inferior lateral side 50, the legs 56, 57 separated by a pocket 52 that is configured to receive a bony structure of an inferior situated vertebra (adjacent to the superior situated vertebra). The third and fourth legs 56 and 57 define first and second lateral sides of the pocket 52 with a curved bottom 63. The first lateral side of the pocket 52 has a first plurality of teeth, serrations or ridged surfaces 61 (collectively, teeth) along its length. The first plurality of teeth 61 provide for connection to a first portion of a bony structure of the inferior vertebra. The second lateral side of the pocket 52 has a second plurality of teeth, serrations or ridged surfaces 62 (collectively, teeth) along its length. The second plurality of teeth 62 provide for connection to a second portion of the bony structure of the inferior situated vertebra. The sides of the pocket 52 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony vertebral structure.

The flexible spinal spacer 40 is thus configured to provide for various degrees of angulation, flexion, extension and/or compression. Thus, the present flexible spinal spacer allows for controlled movement of the adjacent vertebrae to which it is attached (the superior and inferior situated vertebra), as well as aid in insertion and/or implantation of the flexible spinal spacer.

Referring to FIGS. 7-9, there is shown another embodiment of a flexible interspinous or inter-laminar spinal spacer (processes, transverse and spinous—i.e. flexible spinal spacer) generally designated 80 fashioned in accordance with the principles of the present invention. The flexible spinal spacer 80 is used as an interspinous, inter-laminar, interbody, or interbony spinal spacer and thus is configured to be placed between bony structures of adjacent vertebrae of a spine.

The flexible spinal spacer 80 is formed as a unitary or single-piece body 82 of a biocompatible material. The body 82 is formed in a generally "H" shape and thus and thus defines a first superior lateral side 85, a second superior lateral side 86, a first inferior lateral side 87, a second inferior lateral side 88, a posterior side 83, an anterior side 84, a superior side or end 89, and an inferior side or end 90. It should be appreciated that the flexible spinal spacer may take forms other than an "H" while maintaining the features and/or characteristics of the present invention. The body 82 also has a flex portion 110 disposed between the superior side 89 and the inferior side 90. The flex portion 110 has flexure characteristics/properties that provide for relative movement or motion of the spinal spacer 80 and thus motion or movement between the adjacent vertebrae to which it is connected. The flex portion 110 is configurable to provide for various degrees of angulation and/or compression of the body 82.

The flex portion 110 comprises a first flexure contour 114 (e.g. spring or spring-like contours 114) defined by and in the posterior side 83 of the unitary body 82 and a second flexure contour 118 (e.g. springs or spring-like contours 118) defined by the anterior side 84 of the unitary body 82. In FIGS. 7-9, the first and second flexure contours 114, 118 extend from the superior end 89 to the inferior end 90. It should be appreciated that the shape and/or configuration of the flexure contours 114, 118 may be fashioned differently if desired to achieve angulation, flexion, extension and/or compression of the body 82. A cavity 120 is defined between the flexure contours 114, 118. The number of contours and their configuration may vary depending on the desired amount and/or type of flexure and/or flexure properties.

Additionally, a first cutout, cavity or depression 112 is defined between the lateral sides 86 and 88 at the junction of the flexure contours 114, 118 (flex portion 110), while a second cutout, cavity or depression 116 is defined between the lateral sides 85 and 87 at the junction of the flexure contours 114, 118 (flex portion 110). It should be appreciated that the shape of the cutouts 114, 116 may be fashioned differently than shown to achieve a desired amount and/or type of flexure and/or flexure properties (angulation, flexion, extension and/or compression) of the body 82.

The superior end 89 is formed as a saddle-shape defining first and second legs 94, 96 with leg 94 having the first inferior lateral side 85 and leg 96 having the second inferior lateral side 86, the legs 94, 96 separated by a pocket 92 that is configured to receive a bony structure of a superior situated vertebra. The first and second legs 94 and 96 define first and second lateral sides of the pocket 92 with a curved bottom 99. The first lateral side of the pocket 92 has a first plurality of teeth, serrations or ridged surfaces 97 (collectively, teeth) along its length. The first plurality of teeth 97 provide for connection to a first portion of a bony vertebral structure. The second lateral side of the pocket 92 has a second plurality of teeth, serrations or ridged surfaces 97 (collectively, teeth) along its length. The second plurality of teeth 97 provide for connection to a second portion of the bony structure of the superior situated vertebra. The sides of the pocket 92 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony structure of the superior situated vertebra.

The inferior end 90 is formed as a saddle-shape defining third and fourth legs 102, 104, with leg 102 having the first inferior lateral side 87 and leg 104 having the second inferior lateral side 88, the legs 102, 104 separated by a pocket 100 that is configured to receive a bony structure of an inferior situated vertebra (adjacent to the superior situated vertebra). The third and fourth legs 102 and 104 define first and second lateral sides of the pocket 100 with a curved bottom 107. The first lateral side of the pocket 100 has a first plurality of teeth, serrations or ridged surfaces 105 (collectively, teeth) along its length. The first plurality of teeth 105 provide for connection to a first portion of a bony structure of the inferior vertebra. The second lateral side of the pocket 100 has a second plurality of teeth, serrations or ridged surfaces 106 (collectively, teeth) along its length. The second plurality of teeth 106 provide for connection to a second portion of the bony structure of the inferior situated vertebra. The sides of the pocket 100 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony vertebral structure.

The flexible spinal spacer 80 is thus configured to provide for various degrees of angulation, flexion, extension and/or compression. Thus, the present flexible spinal spacer allows for controlled movement of the adjacent vertebrae to which it is attached (the superior and inferior situated vertebra), as well as aid in insertion and/or implantation of the flexible spinal spacer.

Figure 10:
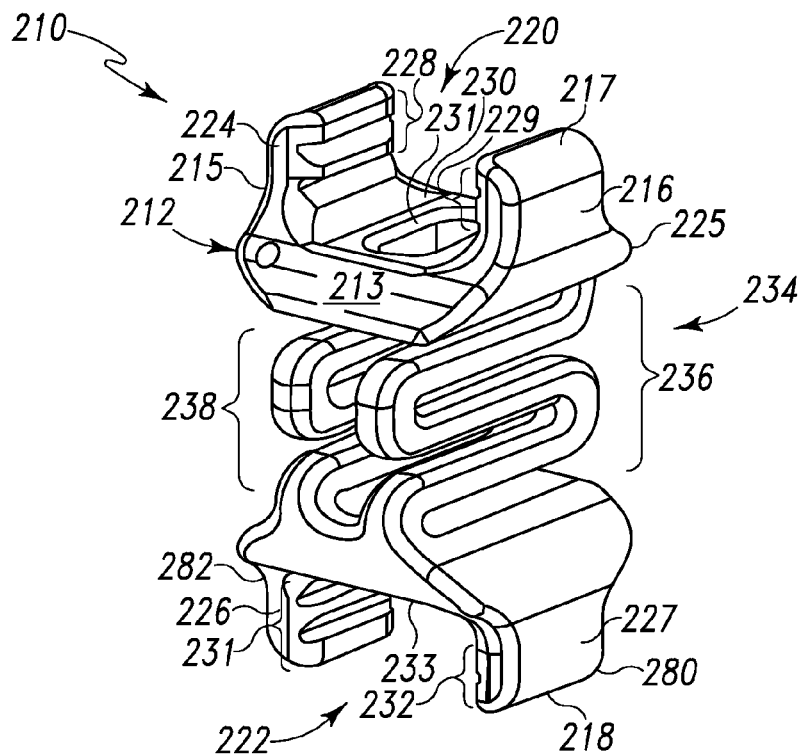
FIG. 10 is an isometric view of another embodiment of a flexible interspinous/inter-laminar spinal spacer (processes, transverse & spinous—i.e. flexible spinal spacer)
Figure 11:
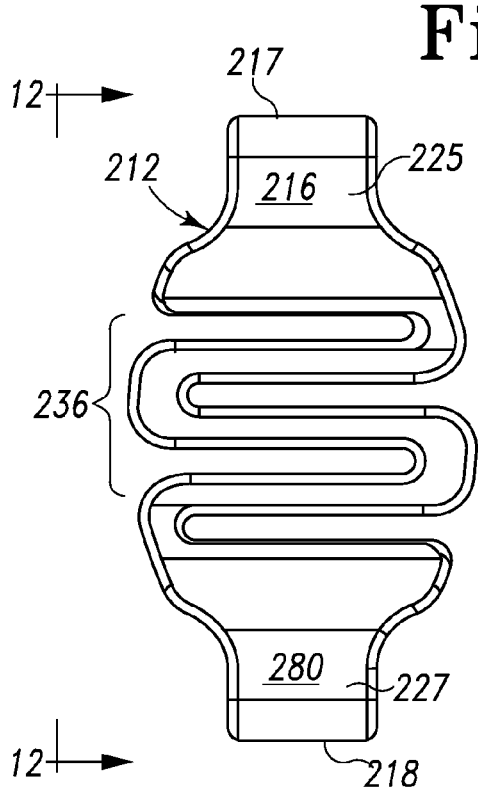
FIG. 11 is a front view of the flexible spinal spacer of FIG. 10.
Figure 12:
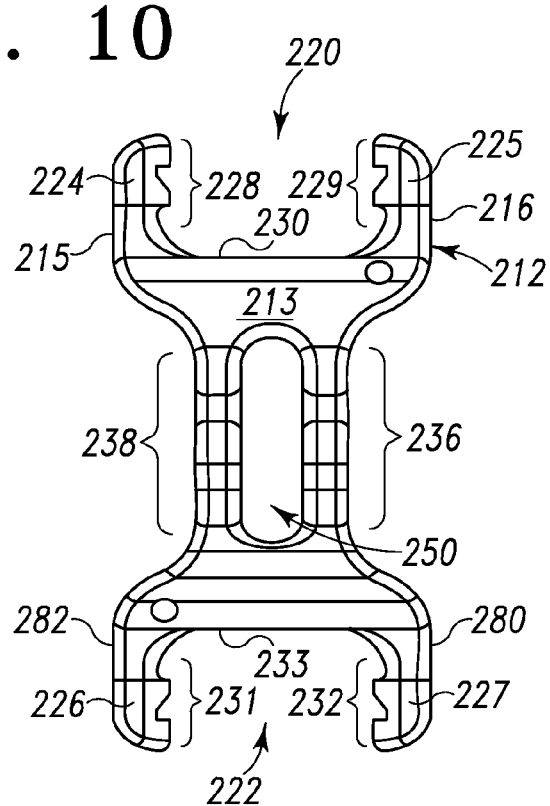
FIG. 12 is a side view of the flexible spinal spacer of FIG. 10 taken along line 12-12 of FIG. 11.

Referring to FIGS. 10-12, there is shown another embodiment of a flexible interspinous or inter-laminar spinal spacer (processes, transverse and spinous—i.e. flexible spinal spacer) generally designated 210 fashioned in accordance with the principles of the present invention. The flexible spinal spacer 210 is used as an interspinous, inter-laminar, interbody, or interbony spinal spacer and thus is configured to be placed between bony structures of adjacent vertebrae of a spine.

The flexible spinal spacer 210 is formed as a unitary or single-piece body 212 of a biocompatible material. The body 212 defines a first superior lateral side 216, a second superior lateral side 215, a first inferior lateral side 280, a second inferior lateral side 282, a posterior side 213, an anterior side opposite the posterior side, a superior side or end 217, and an inferior side or end 218. It should be appreciated that the flexible spinal spacer may take forms other than an "H" while maintaining the features and/or characteristics of the present invention. The body 212 also has a flex portion 234 disposed between the superior side 217 and the inferior side 218. The flex portion 234 has flexure characteristics/properties that provide for relative movement or motion of the spinal spacer 210 and thus motion or movement between the adjacent vertebrae to which it is connected. The flex portion 234 is configurable to provide for various degrees of angulation and/or compression of the body 212.

The flex portion 234 comprises a first flexure contour 236 (e.g. a spring or spring-like contours) defined by and in a lateral side of the unitary body 212 and a second flexure contour 238 (e.g. a spring or spring-like contours) defined by and in the other lateral of the unitary body 212. It should be appreciated that the shape and/or configuration of the flexure contours 236, 238 may be fashioned differently if desired to achieve angulation, flexion, extension and/or compression of the body 212. A cavity 250 is defined between the flexure contours 236, 238. The number of contours and their configuration may vary depending on the desired amount and/or type of flexure and/or flexure properties.

The superior end 217 is formed as a saddle-shape defining first and second legs 224, 225 separated by a pocket 220 that is configured to receive a bony structure of a superior situated vertebra. The first and second legs 224 and 226 define first and second lateral sides of the pocket 220 with a curved bottom 230 having an opening 231 therein. The first lateral side of the pocket 220 has a first plurality of teeth, serrations or ridged surfaces 228 (collectively, teeth) along its length. The first plurality of teeth 228 provide for connection to a first portion of a bony vertebral structure. The second lateral side of the pocket 220 has a second plurality of teeth, serrations or ridged surfaces 229 (collectively, teeth) along its length. The second plurality of teeth 229 provide for connection to a second portion of the bony structure of the superior situated vertebra. The sides of the pocket 220 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony structure of the superior situated vertebra.

The inferior end 218 is formed as a saddle-shape defining third and fourth legs 226, 227 separated by a pocket 222 that is configured to receive a bony structure of an inferior situated vertebra (adjacent to the superior situated vertebra). The third and fourth legs 226 and 227 define first and second lateral sides of the pocket 222 with a curved bottom 223 having an opening therein (not seen). The first lateral side of the pocket 222 has a first plurality of teeth, serrations or ridged surfaces 231 (collectively, teeth) along its length. The first plurality of teeth 231 provide for connection to a first portion of a bony structure of the inferior vertebra. The second lateral side of the pocket 222 has a second plurality of teeth, serrations or ridged surfaces 232 (collectively, teeth) along its length. The second plurality of teeth 232 provide for connection to a second portion of the bony structure of the inferior situated vertebra. The sides of the pocket 222 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony vertebral structure.

The flexible spinal spacer 210 is thus configured to provide for various degrees of angulation, flexion, extension and/or compression. Thus, the present flexible spinal spacer allows for controlled movement of the adjacent vertebrae to which it is attached (the superior and inferior situated vertebra), as well as aid in insertion and/or implantation of the flexible spinal spacer.

Figure 13:
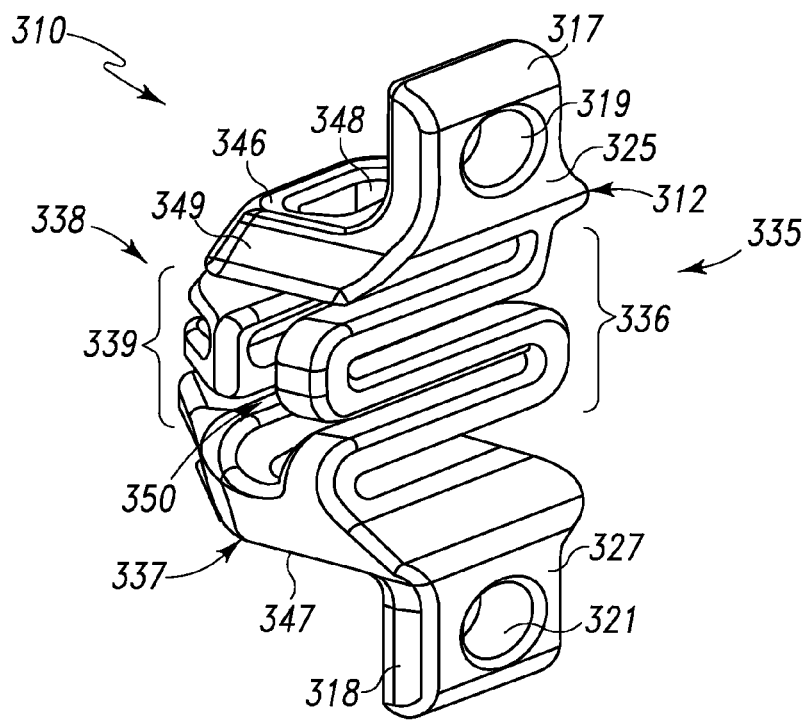
FIG. 13 is an isometric view of another embodiment of a flexible interspinous/inter-laminar spinal spacer (processes, transverse & spinous—i.e. flexible spinal spacer)
Figures 14, 15:
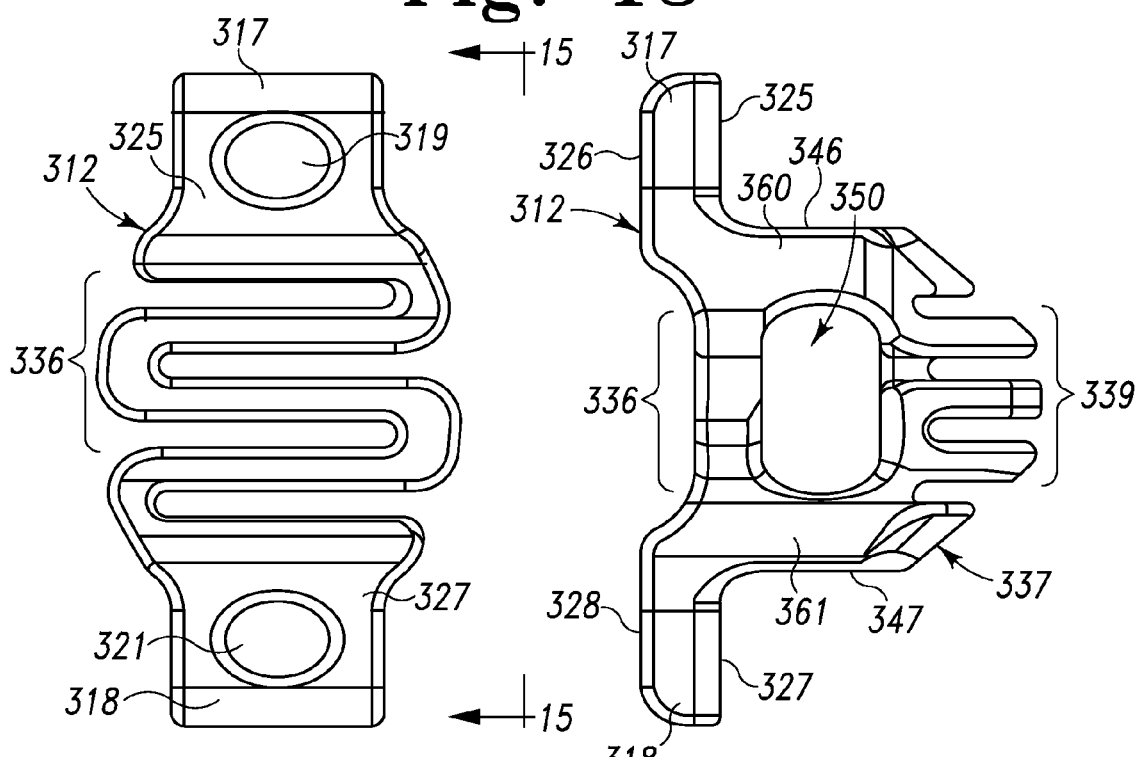
FIG. 14 is a front view of the flexible spinal spacer of FIG. 13.
FIG. 15 is a side view of the flexible spinal spacer of FIG. 13 taken along line 15-15 of FIG. 13.

Referring to FIGS. 13-15, there is shown another embodiment of a flexible interspinous or inter-laminar spinal spacer (processes, transverse and spinous—i.e. flexible spinal spacer) generally designated 310 fashioned in accordance with the principles of the present invention. The flexible spinal spacer 310 is used as an interspinous, inter-laminar, interbody, or interbony spinal spacer and thus is configured to be placed between bony structures of adjacent vertebrae of a spine.

The flexible spinal spacer 310 is formed as a unitary or single-piece body 312 of a biocompatible material. The body 312 has a first flange 317 defining a lateral wall 325 and a second flange 318 defining a lateral wall 327. The first flange 317 has a bore 319 while the second flange 318 has a bore 321. Each bore 319 and 321 allows the reception of bone screw, staple, sutures or other fastening or holding device for securement to the spinous processes. The body 312 also has a flex portion 335 disposed between the first and second flanges 317, 318. The flex portion 335 has flexure characteristics/properties that provide for relative movement or motion of the spinal spacer 310 and thus motion or movement between the adjacent vertebrae to which it is connected. The flex portion 335 is configurable to provide for various degrees of angulation and/or compression of the body 312.

The flex portion 335 comprises a flexure contour 339 (e.g. a spring or spring-like contours) defined by and in a lateral side of the unitary body 312. It should be appreciated that the shape and/or configuration of the flexure contour 339 may be fashioned differently if desired to achieve angulation, flexion, extension and/or compression of the body 312. The number of contours and their configuration may vary depending on the desired amount and/or type of flexure and/or flexure properties.

The body 312 also defines a bullet nose or projection 337 that extends from a first arm 360 and a second arm 361, with the first and second arms 360, the bullet nose 337 and the flex portion 335 defining a cavity 350. The bullet nose 337 includes a plurality of protrusions 339 that are designed to pierce through the interspinous ligament so that the ligament can remain intact for holding the implant in place. The number of protrusions and their configuration may vary as desired.

The flexible spinal spacer 310 is thus configured to provide for various degrees of angulation, flexion, extension and/or compression. Thus, the present flexible spinal spacer allows for controlled movement of the adjacent vertebrae to which it is attached (the superior and inferior situated vertebra), as well as aid in insertion and/or implantation of the flexible spinal spacer.

Figure 16:
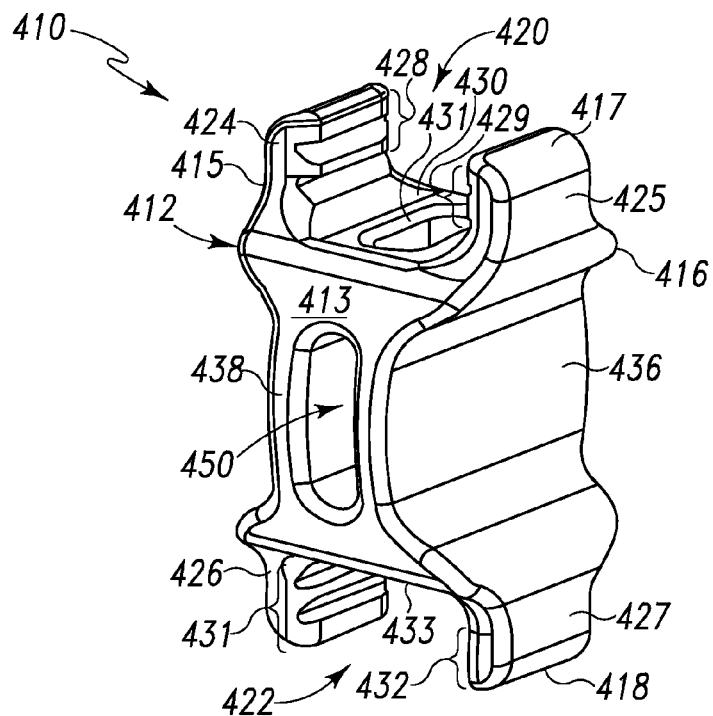
FIG. 16 is an isometric view of a static interspinous/inter-laminar spinal spacer (processes, transverse & spinous—i.e. static spinal spacer)
Figure 17:
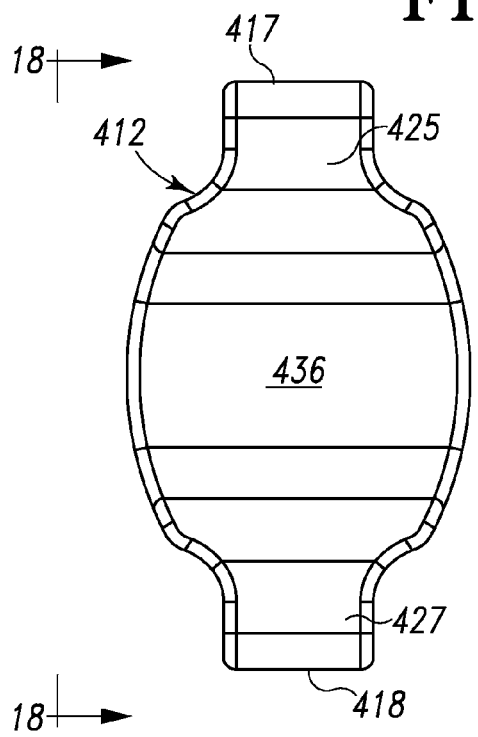
FIG. 17 is a front view of the static spinal spacer of FIG. 16.
Figure 18:
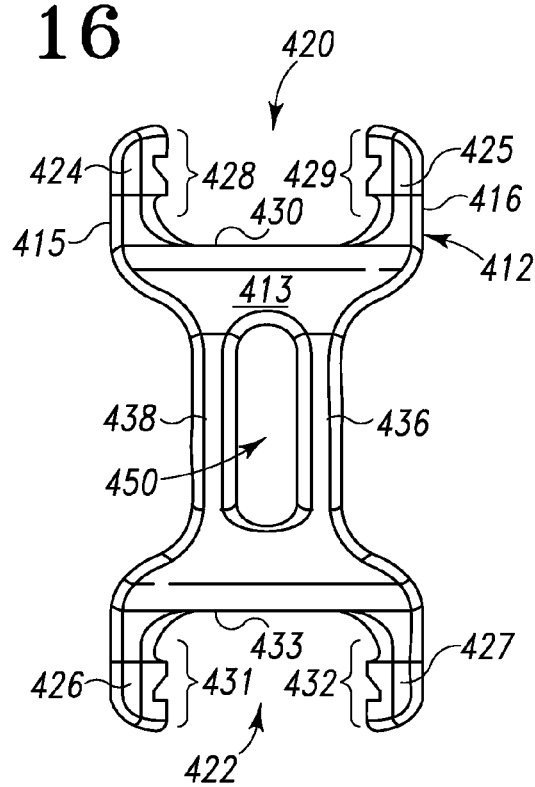
FIG. 18 is a side view of the static spinal spacer of FIG. 16 taken along line 18-18 of FIG. 17.

Referring to FIGS. 16-18, there is shown an embodiment of a static interspinous or inter-laminar spinal spacer (processes, transverse and spinous—i.e. static spinal spacer) generally designated 410 fashioned in accordance with the principles of the present invention. The static spinal spacer 410 is used as an interspinous, inter-laminar, interbody, or interbony spinal spacer and thus is configured to be placed between bony structures of adjacent vertebrae of a spine.

The static spinal spacer 410 is formed as a unitary or single-piece body 412 of a biocompatible material. The body 412 defines a first superior lateral side 416, a second superior lateral side 415, a first inferior lateral side 427, a second inferior lateral side 426, a posterior side 413, an anterior side opposite the posterior side, a superior side or end 417, and an inferior side or end 418. It should be appreciated that the flexible spinal spacer may take forms other than an "H" while maintaining the features and/or characteristics of the present invention.

The superior end 417 is formed as a saddle-shape defining first and second legs 424, 425 separated by a pocket 420 that is configured to receive a bony structure of a superior situated vertebra. The first and second legs 424 and 425 define first and second lateral sides of the pocket 420 with a curved bottom 430 having an opening 431 therein. The first lateral side of the pocket 420 has a first plurality of teeth, serrations or ridged surfaces 428 (collectively, teeth) along its length. The first plurality of teeth 428 provide for connection to a first portion of a bony vertebral structure. The second lateral side of the pocket 420 has a second plurality of teeth, serrations or ridged surfaces 429 (collectively, teeth) along its length. The second plurality of teeth 429 provide for connection to a second portion of the bony structure of the superior situated vertebra. The sides of the pocket 420 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony structure of the superior situated vertebra.

The inferior end 418 is formed as a saddle-shape defining third and fourth legs 426, 427 separated by a pocket 422 that is configured to receive a bony structure of an inferior situated vertebra (adjacent to the superior situated vertebra). The third and fourth legs 426 and 427 define first and second lateral sides of the pocket 422 with a curved bottom 433 having an opening therein (not seen). The first lateral side of the pocket 422 has a first plurality of teeth, serrations or ridged surfaces 431 (collectively, teeth) along its length. The first plurality of teeth 431 provide for connection to a first portion of a bony structure of the inferior vertebra. The second lateral side of the pocket 422 has a second plurality of teeth, serrations or ridged surfaces 432 (collectively, teeth) along its length. The second plurality of teeth 432 provide for connection to a second portion of the bony structure of the inferior situated vertebra. The sides of the pocket 422 may or may not be textured (shown in the figures as not textured) and/or may or may not include teeth, serrations, or ridged surfaces (shown in the figures with teeth, serrations, or ridged surfaces) in order to secure the superior end of the spinal spacer to the bony vertebral structure.

The body 412 has a first sidewall 436 disposed between the first and second legs 424, 425 and the third and fourth legs 426, 427, and a second sidewall 438 disposed between the first and second legs 424, 425 and the third and fourth legs 426, 427. The first and second sidewalls 436, 438 are rigid thus defining a static spinal spacer. A cavity 450 is disposed between the first and second sidewalls 436, 438.

Figure 19:
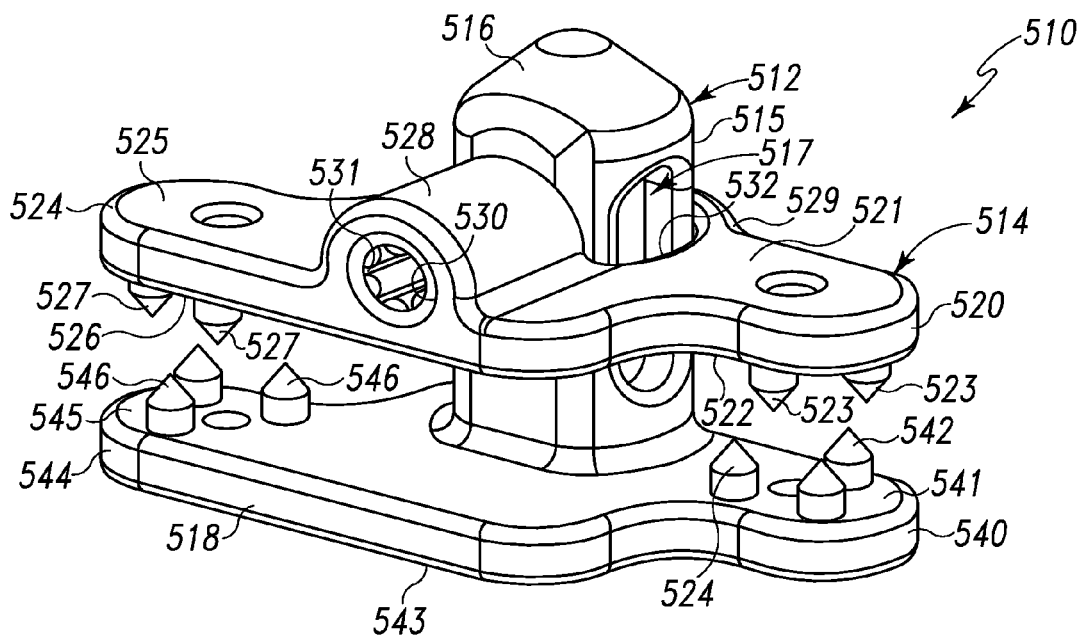
FIG. 19 is an isometric view of another embodiment of a static interspinous/inter-laminar spinal spacer (processes, transverse & spinous—i.e. static spinal spacer)
Figures 20, 21:
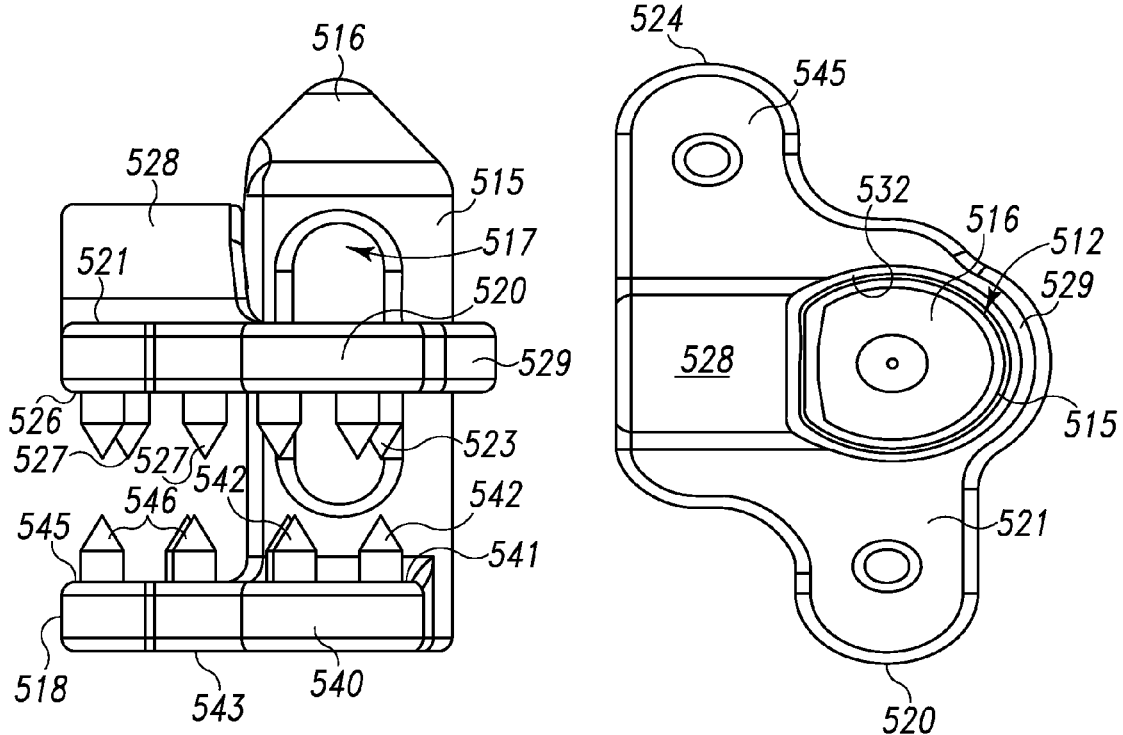
FIG. 20 is a front view of the static spinal spacer of FIG. 19.
FIG. 21 is a side view of the flexible spinal spacer of FIG. 19 taken along line 21-21 of FIG. 20'
Figure 22:
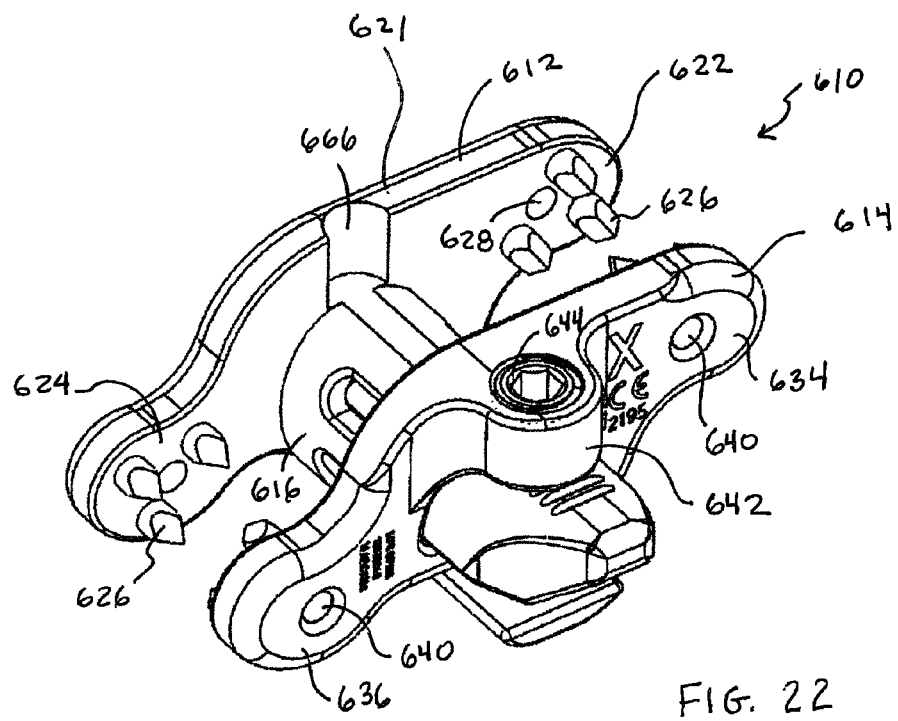
FIG. 22 is a perspective view of an implant according to another embodiment.

Referring now to FIGS. 19-21, there is shown another embodiment of a static interspinous or inter-laminar spinal spacer (processes, transverse and spinous—i.e. static spinal spacer) generally designated 510 fashioned in accordance with the principles of the present invention. The static spinal spacer 510 is used as an interspinous, inter-laminar, interbody, or interbony spinal spacer and thus is configured to be placed between bony structures of adjacent vertebrae of a spine.

The static spinal spacer 510 is formed by a body 512 having a contoured plate 518 defining a lower surface 543 and having a post 515 extending transverse to the contoured plate 518 from an upper surface thereof. The post 515 has a bullet nose or projection 516 that is designed to pierce through the interspinous ligament so that the ligament can remain intact for holding the implant in place, and an interior cavity 517. The contoured plate 518 has a first wing 540 defining an upper surface 541 having a plurality of spikes 542 or other similar features for engaging the spinous process for securement thereof. The contoured plate 518 also has a second wing 544 defining an upper surface 545 having a plurality of spikes 546 or other similar features for engaging the spinous process for securement thereof.

A second contoured plate 514 having a lateral wall is provided for attachment to the post 515. The second contoured plate 514 has a first wing 520 defining a lower surface 522 having a plurality of spikes 523 or other similar features for engaging the spinous process for securement thereof. The second contoured plate 514 has a second wing 524 defining a lower surface 526 having a plurality of spikes 527 or other similar features for engaging the spinous process for securement thereof. The second contoured plate 514 further has a bore 532 that is sized for reception onto the post 515. The bore 532 defines a rounded rear portion 529 that extends about the post 515. The second contoured plate 514 also has an elongated boss 528 having a bore 530 for securement of the second contoured plate 514 onto the post 515. The second contoured plate 514 is movable up and down the post 515 for proper positioning and securement of the second contoured plate 514. The second contoured plate 514 aids in preventing rotation between the components. A set screw 531 is received in the boss bore 530 that engages the post 515 for fixing the second contoured plate 514 relative to the post 515.

Referring now to FIGS. 22-35, various implants or spacers (e.g., spinal spacers or implants) are shown according to various alternative embodiments. Referring to FIGS. 22-26, an implant 610 is shown according to one embodiment. In one embodiment, implant 610 includes a first plate 612, a second plate 614, and a post 616 (e.g., a core, elongated member). First plate 612 and post 616 may form an implant body. First plate 612 and post 616 may be separate components coupled together or may be integrally formed. In some embodiments, implant 610 is usable as an interspinous, inter-laminar, interbody, or interbony spinal spacer, and thus is configured to be placed between bony structures of adjacent vertebrae of a spine.

Figure 23:
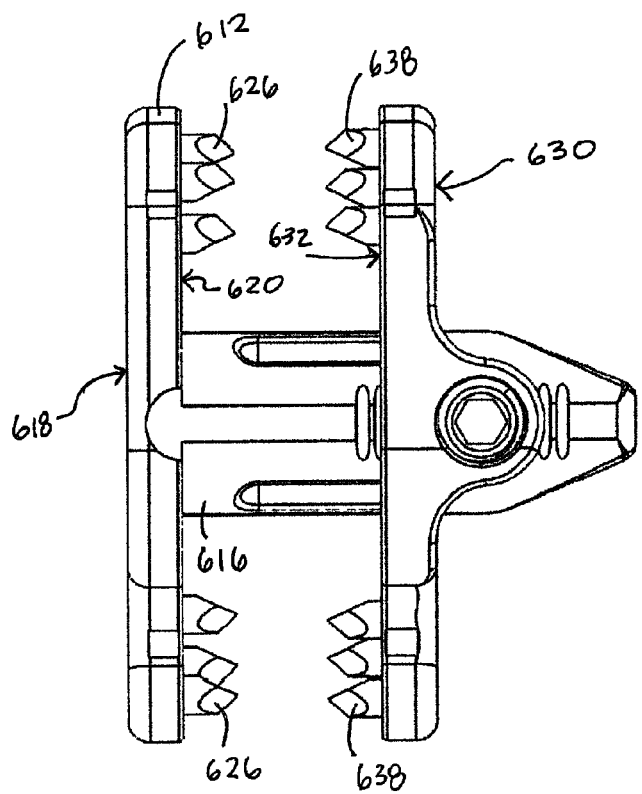
FIG. 23 is a front view of the implant of FIG. 22 according to one embodiment.
Figure 27:
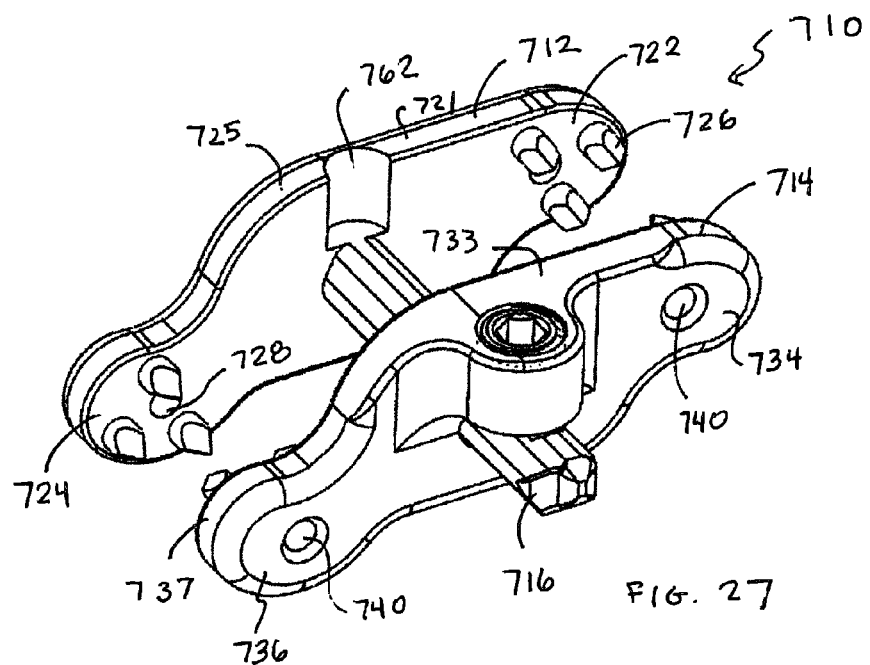
FIG. 27 is a perspective view of an implant according to another embodiment.

First plate 612 is fixed in position relative to post 616, and post 616 extends transversely relative to first plate 612. Second plate 614 is adjustable along post 616 to accommodate different sized applications. As shown in FIG. 23, first plate 612 and second plate 614 are generally parallel. In other embodiments, first plate 612 and second plate 614 (or portions thereof) may be configured in a non-parallel (e.g., canted, angled) relationship.

According to one embodiment, first plate 612 includes an outer surface 618 and an inner surface 620. In some embodiments, inner surface 620 defines a generally continuous, flat, and/or planar surface, while in other embodiments, inner surface 620 defines a discontinuous, contoured, and/or non-planar surface (e.g., defining one or more recesses, or irregular surface contours). First plate 612 further includes a central portion 621. A first wing 622 extends in a first direction (e.g., upward) from central portion 621, and a second wing 624 extends in a second direction (e.g., downward) from central portion 621. First wing 622 and/or second wing 624 may include a plurality of projections, or spikes 626 extending outward from inner surface 620. In one embodiment, spikes 626 extend in a generally perpendicular manner outward from inner surface 620, while in other embodiments, spikes 626 extend in a non-perpendicular (e.g., angled) manner outward from inner surface 620 (or edge portions thereof). According to one embodiment, spikes 626 are configured to engage bone material (e.g., one or more spinous processes) to secure implant 610 in a desired configuration. In some embodiments, first plate 612 further includes one or more through-holes or apertures 628. In one embodiment, first wing 622 and/or second wing 624 each include one or more apertures 628. Apertures 628 may enable the passage of bone and/or bone growth material therethrough, and may be positioned adjacent spikes 626. In one embodiment, first plate 612 includes a groove 666 extending from an edge portion of first plate 612 to (or proximate to) an end of post 616. Groove 666 is usable to receive instrumentation or tooling to facilitate placement and/or positioning or adjustment of implant 610.

According to one embodiment, second plate 614 includes an outer surface 630 and an inner surface 632. In some embodiments, inner surface 632 defines a generally continuous, flat, and/or planar surface, while in other embodiments, inner surface 632 defines a discontinuous, contoured, and/or non-planar surface (e.g., defining one or more recesses, or irregular surface contours). Second plate 614 further includes a central portion 633. A first wing 634 extends in a first direction (e.g., upward) from central portion 633, and a second wing 636 extends in a second direction (e.g., downward) from central portion 633. First wing 634 and/or second wing 636 may include a plurality of projections, or spikes 638 extending outward from inner surface 632. In one embodiment, spikes 638 extend in a generally perpendicular manner outward from inner surface 632, while in other embodiments, spikes 638 extend in a non-perpendicular (e.g., angled) manner outward from inner surface 632 (or edge portions thereof). According to one embodiment, spikes 638 are configured to engage bone material (e.g., one or more spinous processes) to secure implant 610 in a desired configuration. In some embodiments, second plate 614 further includes one or more through-holes or apertures 640. In one embodiment, first wing 634 and/or second wing 636 each include one or more apertures 640. Apertures 640 may enable the passage of bone and/or bone growth material therethrough, and may be positioned adjacent spikes 638. Second plate 614 further includes a bore 646 configured to receive all or a portion of post 616 and enable slidable adjustment of second plate 614 along post 616.

In some embodiments, second plate 614 further includes a raised portion or boss 642. Boss 642 is configured to receive fastener or adjustment screw 644 (e.g., a set screw) such that screw 644 can be threaded into and out of boss 642 to engage and/or disengage post 616 and secure second plate 614 in position relative to post 616 and first plate 612.

Referring to FIGS. 24 and 25, first plate 612 and second plate 614 define contoured peripheral edges configured to facilitate insertion and adjustment of implant 610. For example, first plate 612 includes a peripheral edge 625 extending between all or portions of outer surface 618 and inner surface 620 of first plate 612. Similarly, second plate 614 includes peripheral edge 637 extending between outer surface 630 and inner surface 632 of second plate 614. Edges 625, 637 may define various peripheral contours for first and second plates 612, 614, including curved, straight, or other contours extending about all or a portion of first and second plates 612, 614.

Referring to FIG. 25, first wing 622 of first plate 612 extends from a first side of central portion 621, and second wing 624 extends from a second side of central portion 621, such that first and second wings 622, 624 are offset relative to one another and a midpoint of central portion 621. In other embodiments, first and second wings 622, 624 may be offset to the same side of central portion 621. In one embodiment, edge 625 of first plate 612 defines an undercut area 662 between central portion 621 and second wing 624 and a protruding area 664 at central portion 621. In one embodiment, first wing 634 and central portion 633 of second plate 214 define a continuous straight portion of edge 637 (see FIG. 24), while second wing 636 is offset beyond the peripheral edge of central portion 633. First and second plates 612, 614 may have a same or similar peripheral contour about all or a portion of the perimeter of the plates (e.g., a mirror-image).

In some embodiments, post 616 is an elongated member extending from first plate 612. Post 616 includes a first end 648 adjacent first plate 612 and an opposite second end 650. One or more projections or ridges 652 extend along a length of post 616 between first end 648 and second end 650. As shown in FIGS. 22-26, all or a portion of post 616 (e.g., a cross sectional portion) is received in bore 646 to enable adjustment (e.g., sliding adjustment) of second plate 614 relative to first plate 612. Once second plate 614 is in a desired position, screw 644 is tightened to engage ridges 652 (or the corresponding recesses) and secure second plate 614 in position.

As shown in FIGS. 24 and 26, post 616 may include a first portion 654 and a second portion 656. Portions 654 and 656 may be elongated portions that extend parallel to one another and define a channel 660 therebetween. In one embodiment, first portion 654 forms a "C" shape and second portion 6565 forms a solid "D" shape. In other embodiments, first and second portions 654, 656 may take other suitable shapes. As shown in FIG. 24, in one embodiment, first portion 654 is received within bore 646 of second plate 614 and second portion 656 extends to the outside of second plate 614. An elongated aperture may extend through first portion 654 and facilitate placement of bone growth material. First portion 654 and second portion 656 may in some embodiments provide a split-post configuration, such that when first plate 712 and post 716 are positioned in place, first portion 754 is resting on or adjacent to anatomy and provides a type of shield or protection relative to the anatomy, such that second plate 714 may more easily be slid onto second portion 756.

Referring to FIGS. 27-31, an implant 710 is shown according to one embodiment. In one embodiment, implant 710 includes a first plate 712, a second plate 714, and a post 716 (e.g., a core, elongated member). First plate 712 and post 716 may form an implant body. First plate 712 and post 716 may be separate components coupled together or may be integrally formed. In some embodiments, implant 710 is usable as an interspinous, inter-laminar, interbody, or inter-bony spinal spacer, and thus is configured to be placed between bony structures of adjacent vertebrae of a spine.

Figure 28:
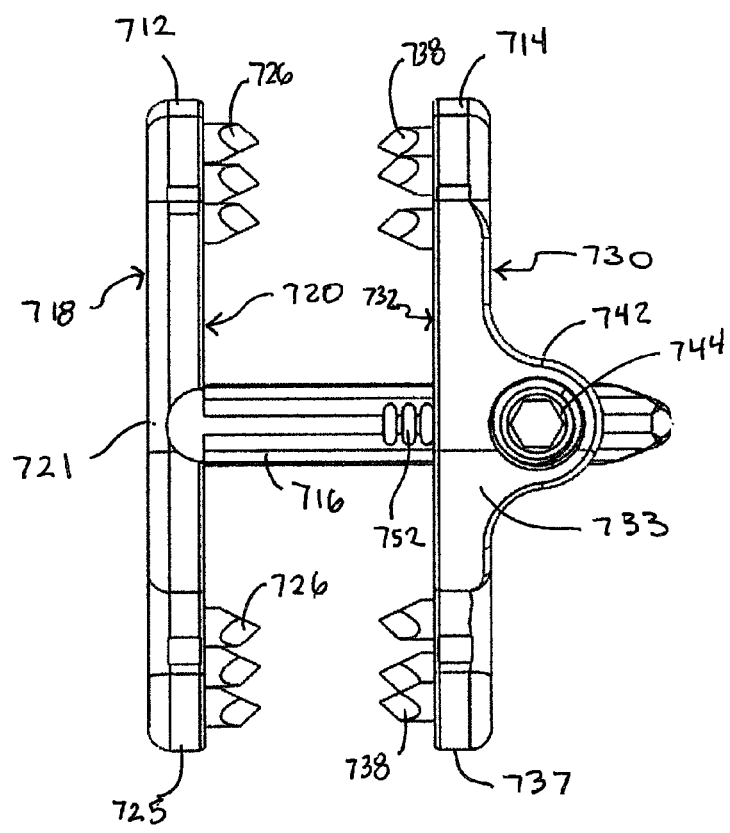
FIG. 28 is a front view of the implant of FIG. 27 according to one embodiment.

First plate 712 is fixed in position relative to post 716, and post 716 extends transversely relative to first plate 712. Second plate 714 is adjustable along post 716 to accommodate different sized applications. As shown in FIG. 28, first plate 712 and second plate 714 are generally parallel. In other embodiments, first plate 712 and second plate 714 (or portions thereof) may be configured in a non-parallel (e.g., canted, angled) relationship.

According to one embodiment, first plate 712 includes an outer surface 718 and an inner surface 720. In some embodiments, inner surface 720 defines a generally continuous, flat, and/or planar surface, while in other embodiments, inner surface 720 defines a discontinuous, contoured, and/or non-planar surface (e.g., defining one or more recesses, or irregular surface contours). First plate 712 further includes a central portion 721. A first wing 722 extends in a first direction (e.g., upward) from central portion 721, and a second wing 724 extends in a second direction (e.g., downward) from central portion 721. First wing 722 and/or second wing 724 may include a plurality of projections, or spikes 726 extending outward from inner surface 720. In one embodiment, spikes 726 extend in a generally perpendicular manner outward from inner surface 732, while in other embodiments, spikes 626 extend in a non-perpendicular (e.g., angled) manner outward from inner surface 720 (or edge portions thereof). According to one embodiment, spikes 726 are configured to engage bone material (e.g., one or more spinous processes) to secure implant 710 in a desired configuration. In some embodiments, first plate 712 further includes one or more through-holes or apertures 728. In one embodiment, first wing 722 and/or second wing 724 each include one or more apertures 728. Apertures 728 may enable the passage of bone and/or bone growth material therethrough, and may be positioned adjacent spikes 726. In one embodiment, first plate 712 includes a groove 762 extending from an edge portion of first plate 712 to (or proximate to) an end of post 716. Groove 762 is usable to receive instrumentation or tooling to facilitate placement and/or positioning or adjustment of implant 710.

According to one embodiment, second plate 714 includes an outer surface 730 and an inner surface 732. In some embodiments, inner surface 732 defines a generally continuous, flat, and/or planar surface, while in other embodiments, inner surface 732 defines a discontinuous, contoured, and/or non-planar surface (e.g., defining one or more recesses, or irregular surface contours). Second plate 714 further includes a central portion 733. A first wing 734 extends in a first direction (e.g., upward) from central portion 733, and a second wing 736 extends in a second direction (e.g., downward) from central portion 733. First wing 734 and/or second wing 736 may include a plurality of projections, or spikes 738 extending outward from inner surface 732. In one embodiment, spikes 738 extend in a generally perpendicular manner outward from inner surface 732, while in other embodiments, spikes 738 extend in a non-perpendicular (e.g., angled) manner outward from inner surface 732 (or edge portions thereof). According to one embodiment, spikes 738 are configured to engage bone material (e.g., one or more spinous processes) to secure implant 710 in a desired configuration. In some embodiments, second plate 714 further includes one or more through-holes or apertures 640. In one embodiment, first wing 734 and/or second wing 736 each include one or more apertures 740. Apertures 740 may enable the passage of bone and/or bone growth material therethrough, and may be positioned adjacent spikes 738. Second plate 714 further includes a bore 746 configured to receive all or a portion of post 716 and enable slidable adjustment of second plate 714 along post 716.

In some embodiments, second plate 714 further includes a raised portion or boss 742. Boss 742 is configured to receive fastener or adjustment screw 744 (e.g., a set screw) such that screw 744 can be threaded into and out of boss 742 to engage and/or disengage post 716 and secure second plate 714 in position relative to post 716 and first plate 712.

Figures 29, 30:
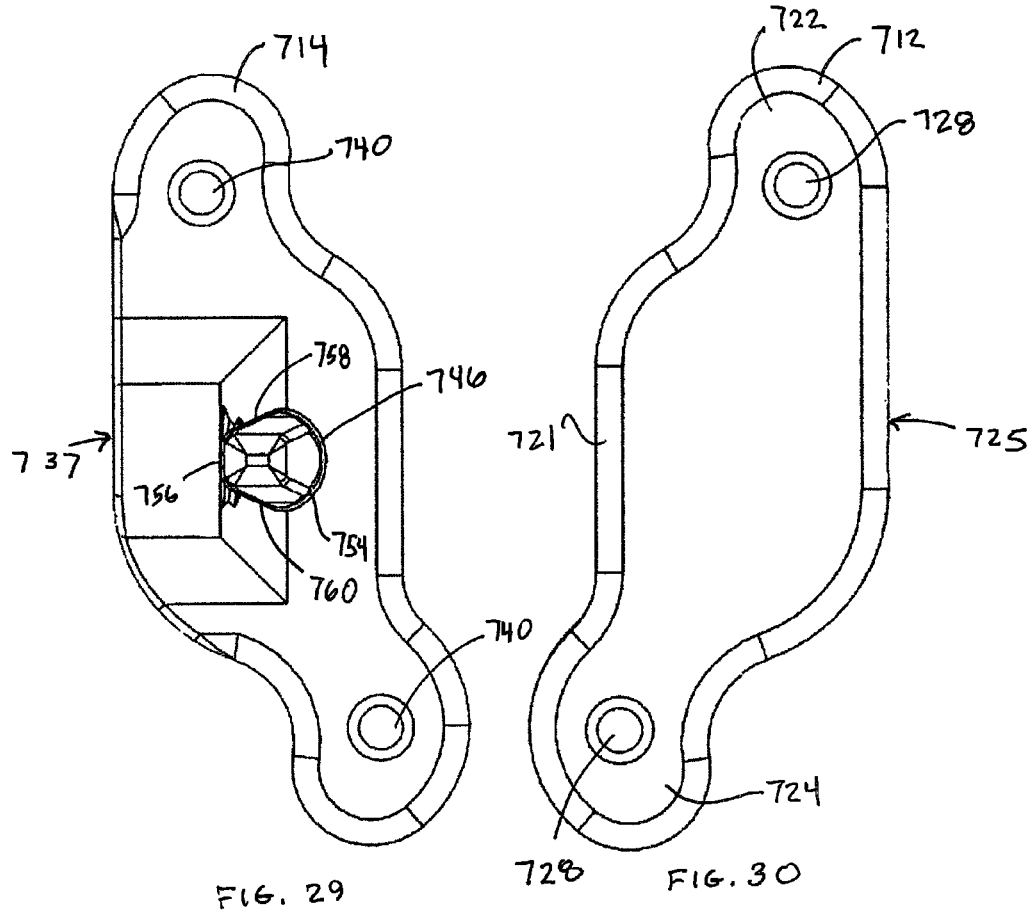
FIGS. 29 and 30 are side views of the implant of FIG. 27 according to one embodiment.

Referring to FIGS. 29 and 30, first plate 712 and second plate 714 define contoured peripheral edges configured to facilitate insertion and adjustment of implant 710. For example, first plate 712 includes a peripheral edge 725 extending between all or portions of outer surface 718 and inner surface 720 of first plate 712. Similarly, second plate 714 includes peripheral edge 737 extending between outer surface 730 and inner surface 732 of second plate 714. Edges 725, 737 may define various peripheral contours for first and second plates 712, 714, including curved, straight, or other contours extending about all or a portion of first and second plates 712, 714.

Referring to FIG. 30, first wing 722 of first plate 712 extends from a first side of central portion 721, and second wing 724 extends from a second side of central portion 721, such that first and second wings 722, 724 are offset relative to one another and a midpoint of central portion 721. In other embodiments, first and second wings 722, 724 may be offset to the same side of central portion 721. In one embodiment, first wing 722 and central portion 721 define a continuous straight portion of edge 725 (see FIG. 30), while second wing 724 is offset beyond the peripheral edge of central portion 721. Second plate 714 may have a same or similar peripheral contour about all or a portion of the perimeter of second plate 714 (e.g., a mirror-image).

In some embodiments, post 716 is an elongated member extending from first plate 712. Post 716 includes a first end 748 adjacent first plate 712 and an opposite second end 750. One or more projections or ridges 752 extend along a length of post 716 between first end 748 and second end 750. As shown in FIGS. 27-31, all or a portion of post 716 is received in bore 746 to enable adjustment (e.g., sliding adjustment) of second plate 714 relative to first plate 712. Once second plate 714 is in a desired position, screw 744 is tightened to engage ridges 752 and secure second plate 714 in position.

Figure 31:
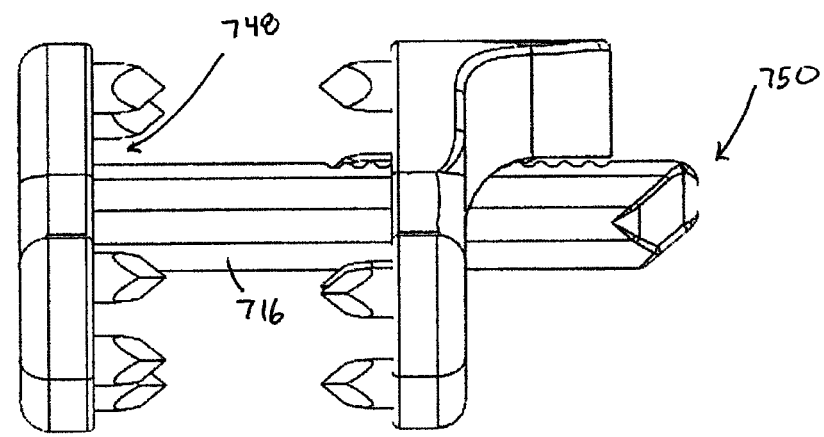
FIG. 31 is a top view of the implant of FIG. 27 according to one embodiment.

As shown in FIGS. 29 and 31, post 716 may include a first side 754, a second side 756, a third side 758, and a fourth side 760. In one embodiment, first side 754 is generally rounded, and third and fourth sides extend from opposite portions of first side 754 to opposite portions of second side 756. Second, third, and fourth sides 756, 758, 760 may be straight or rounded. In one embodiment, third and fourth sides 758 and 760 taper between first side 754 and second side 756. In some embodiments, post 716 is a solid member and second end 750 forms a bullnose to facilitate insertion of implant 710. The bullnose feature may be formed by a plurality of tapered and/or planar surfaces or alternatively by a single curved and tapered surface.

Referring to FIGS. 32-35, an implant 810 is shown according to one embodiment. In one embodiment, implant 810 includes a first plate 812, a second plate 814, and a post 816 (e.g., a core, elongated member). First plate 812 and post 816 may form an implant body. First plate 812 and post 816 may be separate components coupled together or may be integrally formed. In some embodiments, implant 810 is usable as an interspinous, inter-laminar, interbody, or inter-bony spinal spacer, and thus is configured to be placed between bony structures of adjacent vertebrae of a spine.

Figure 32:
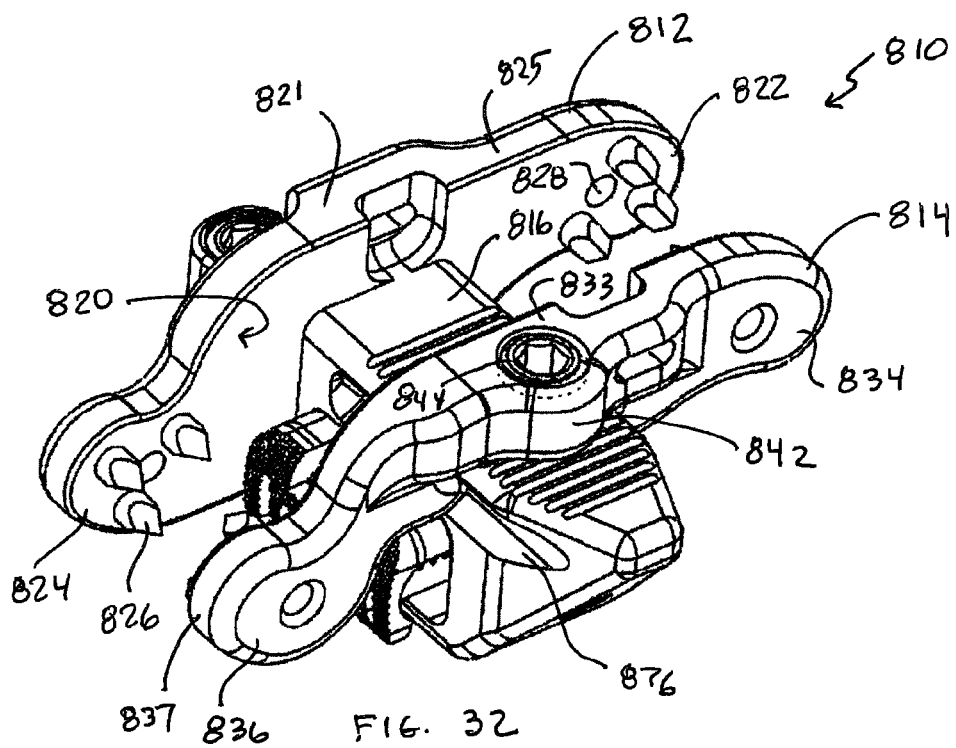
FIG. 32-34 are perspective views of an implant according to another embodiment.

First plate 812 is fixed in position relative to post 816, and post 816 extends transversely relative to first plate 812. Second plate 814 is adjustable along post 816 to accommodate different sized applications. As shown in FIG. 32, first plate 812 and second plate 814 are generally parallel. In other embodiments, first plate 812 and second plate 814 (or portions thereof) may be configured in a non-parallel (e.g., canted, angled) relationship.

According to one embodiment, first plate 812 includes an outer surface 818 and an inner surface 820. In some embodiments, inner surface 820 defines a generally continuous, flat, and/or planar surface, while in other embodiments, inner surface 820 defines a discontinuous, contoured, and/or non-planar surface (e.g., defining one or more recesses, or irregular surface contours). First plate 812 further includes a central portion 821. A first wing 822 extends in a first direction (e.g., upward) from central portion 821, and a second wing 824 extends in a second direction (e.g., downward) from central portion 821. First wing 822 and/or second wing 824 may include a plurality of projections, or spikes 826 extending outward from inner surface 820. In one embodiment, spikes 826 extend in a generally perpendicular manner outward from inner surface 820, while in other embodiments, spikes 826 extend in a non-perpendicular (e.g., angled) manner outward from inner surface 820 (or edge portions thereof). According to one embodiment, spikes 826 are configured to engage bone material (e.g., one or more spinous processes) to secure implant 810 in a desired configuration. In some embodiments, first plate 812 further includes one or more through-holes or apertures 828. In one embodiment, first wing 822 and/or second wing 824 each include one or more apertures 828. Apertures 828 may enable the passage of bone and/or bone growth material therethrough, and may be positioned adjacent spikes 826. In one embodiment, first plate 812 includes a groove 882 extending from an edge portion of first plate 812 toward an end of post 816. Groove 882 is usable to receive instrumentation or tooling to facilitate placement and/or positioning or adjustment of implant 810.

According to one embodiment, second plate 814 includes an outer surface 830 and an inner surface 832. In some embodiments, inner surface 832 defines a generally continuous, flat, and/or planar surface, while in other embodiments, inner surface 832 defines a discontinuous, contoured, and/or non-planar surface (e.g., defining one or more recesses, or irregular surface contours). Second plate 814 further includes a central portion 833. A first wing 834 extends in a first direction (e.g., upward) from central portion 833, and a second wing 836 extends in a second direction (e.g., downward) from central portion 833. First wing 834 and/or second wing 836 may include a plurality of projections, or spikes 838 extending outward from inner surface 832. In one embodiment, spikes 838 extend in a generally perpendicular manner outward from inner surface 832, while in other embodiments, spikes 838 extend in a non-perpendicular (e.g., angled) manner outward from inner surface 832 (or edge portions thereof). According to one embodiment, spikes 838 are configured to engage bone material (e.g., one or more spinous processes) to secure implant 810 in a desired configuration. In some embodiments, second plate 814 further includes one or more through-holes or apertures 840. In one embodiment, first wing 834 and/or second wing 836 each include one or more apertures 840. Apertures 840 may enable the passage of bone and/or bone growth material therethrough, and may be positioned adjacent spikes 838. Second plate 814 further includes a recess 846 configured to receive all or a portion of post 816 and enable slidable adjustment of second plate 814 along post 816.

In some embodiments, second plate 814 further includes a raised portion or boss 842. Boss 842 is configured to receive fastener or adjustment screw 844 (e.g., a set screw) such that screw 844 can be threaded into and out of boss 842 to engage and/or disengage post 816 and secure second plate 814 in position relative to post 816 and first plate 812.

Figure 33:
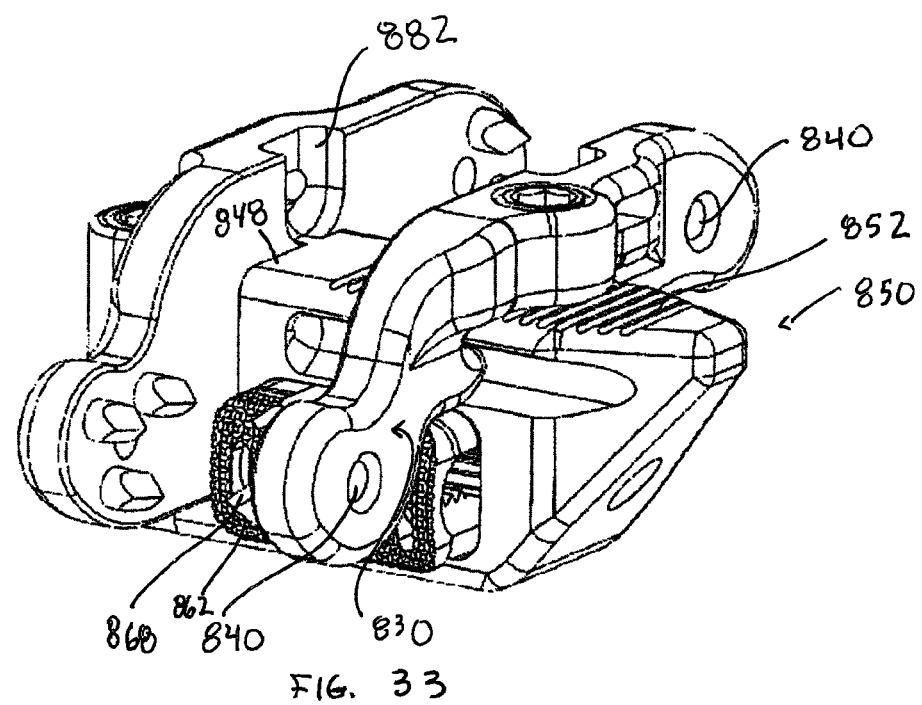
Figure 34:
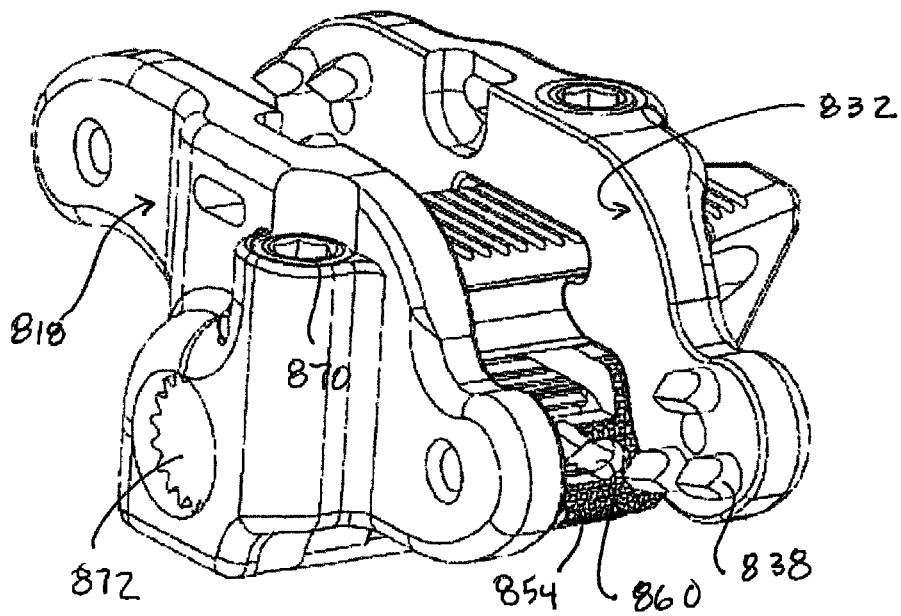
Figure 35:
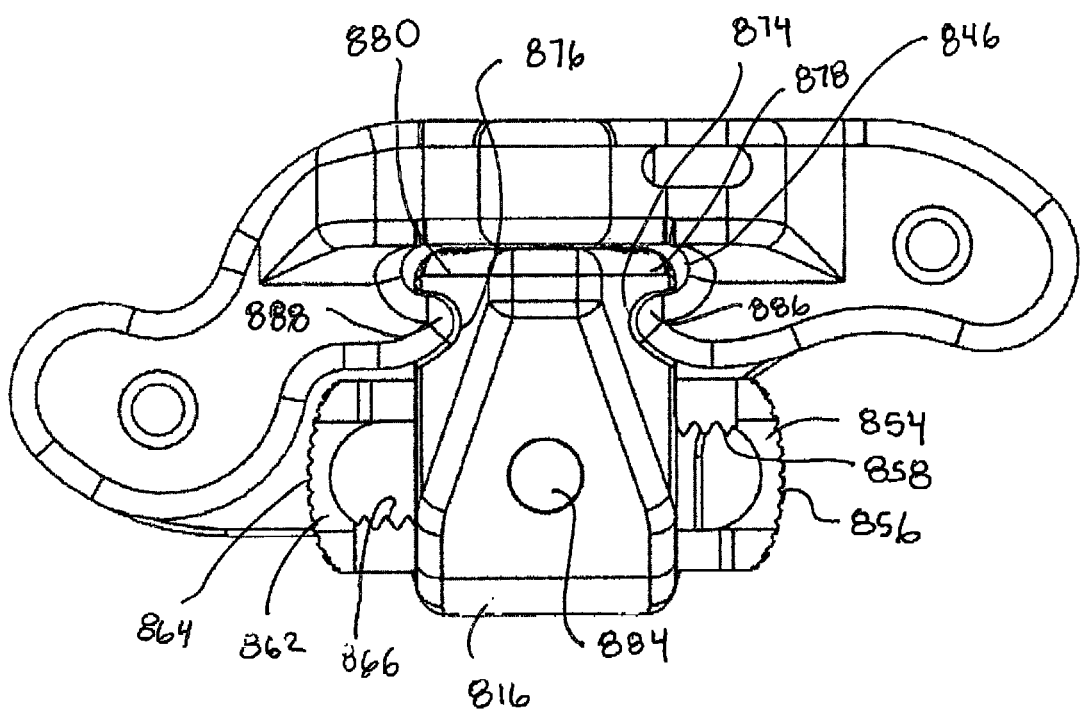
FIG. 35 is a side view of the implant of FIGS. 32-34 according to one embodiment.

Referring to FIGS. 33-35, first plate 812 and second plate 814 define contoured peripheral edges configured to facilitate insertion and adjustment of implant 810. For example, first plate 812 includes a peripheral edge 825 extending between all or portions of outer surface 818 and inner surface 820 of first plate 812. Similarly, second plate 814 includes peripheral edge 837 extending between outer surface 830 and inner surface 832 of second plate 814. Edges 825, 837 may define various peripheral contours for first and second plates 812, 814, including curved, straight, or other contours extending about all or a portion of first and second plates 812, 814.

Referring to FIG. 32, first wing 822 of first plate 812 extends from a first side of central portion 821, and second wing 824 extends from a second side of central portion 821, such that first and second wings 822, 824 are offset relative to one another and a midpoint of central portion 821. In other embodiments, first and second wings 822, 824 may be offset to the same side of central portion 821. In one embodiment, first wing 822 and central portion 821 define a continuous straight portion of edge 825 (see FIGS. 33-35). Second plate 814 may have a same or similar peripheral contour about all or a portion of the perimeter of second plate 814 (e.g., a mirror-image).

In some embodiments, post 816 is an elongated member extending from first plate 812. Post 816 includes a first end 848 adjacent first plate 812 and an opposite second end 850. One or more projections or ridges 852 extend along a length of post 816 between first end 848 and second end 850. As shown in FIG. 35, a portion of post 816 is received in recess 846 to enable adjustment (e.g., sliding adjustment) of second plate 814 relative to first plate 812. Once second plate 814 is in a desired position, screw 844 is tightened to engage ridges 852 and secure second plate 814 in position. In some embodiments, post 816 includes an end bore 884 extending inward from second end 850 of post 816 configured to receive a portion of pinion gear 872.

In one embodiment, second plate 814 travels within grooves in post 816. For example, as shown in FIG. 35, post 816 includes a top groove 874 and a bottom groove 876 that are positioned in opposite surfaces of post 816 and extend along all or a portion of the length of post 816. Grooves 874 and 876 partially define projections 878 and 880 that are received in recess 846 in second plate 814. Likewise, second plate 814 includes projections 886, 888 that are received in top and bottom grooves 874, 876. Utilizing the groove/projection interface shown in FIG. 35 enables, among other things, insertion of second plate 814 from a frontal direction (e.g., extending transversely outward from ridges 852), rather than along the longitudinal axis of post 816.

In some embodiments, post 816 provides an adjustable height feature such that adjustable supports can be moved toward and away from post 816 to provide an adjustable desired support height. For example, referring to FIG. 35, in one embodiment, post 816 includes first and second wedging members 854, 862 (e.g., support members) that are moveable outward relative to post 816. First wedging member 854 includes a support surface 856, a rack 858 and aperture 860. Second wedging member 862 includes a support surface 864, a rack 866, and aperture 868. Support surfaces 856, 864 are configured to engage adjacent bone structures. In one embodiment, support surfaces 856, 864 move linearly in generally opposite directions transversely relative to post 816. In other embodiments, support surfaces 856, 864 move in a nonlinear manner or in other directions. Apertures 860, 868 may facilitate receipt of bone growth material within implant 810.

Rack 858 extends generally transversely from support surface 856, and includes a number of parallel gear teeth. The height of rack 858 in some embodiments limits the amount of expansion that can be provided by first wedging member 854. A pinion gear 872 is received within first plate 812 and extends generally parallel to and/or within post 816. Pinion gear 872 is rotatable within first plate 812 and includes a number of gear teeth extending about pinion gear 872. Pinion gear 872 engages rack 858 such that a rotation of pinion gear 872 causes a corresponding translational movement of first wedging member 854 in an inward or outward direction. Second wedging member 862 has a similar configuration to first wedging member 854.

An adjustment screw 870 is received in second plate 814 and is operationally coupled (e.g., via a worm gear transmission) to pinion gear 872 such that rotation of screw 870 causes a corresponding rotation of pinion gear 872, which in turn causes a corresponding translational movement of first and second wedging members 854, 862 toward or away from each other. As shown in FIGS. 34-35, racks 858, 866 engage opposite sides of pinion gear 872 such that wedging members 854, 862 move equal distances. In some embodiments, implant 810 provides for adjustment of first and second wedging members 854, 862 using an adjustment mechanism similar to that disclosed in U.S. Pat. No. 8,231, 656, which is incorporated herein by reference in its entirety.

Figure 36:
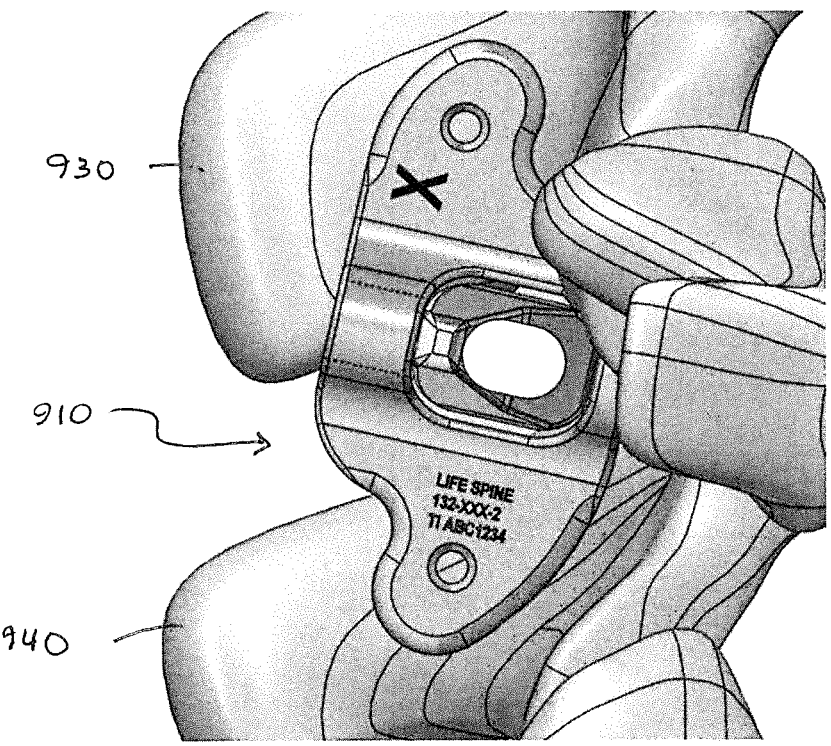
FIG. 36 is a side view of an implant in an implanted position according to one embodiment.
Figure 37:
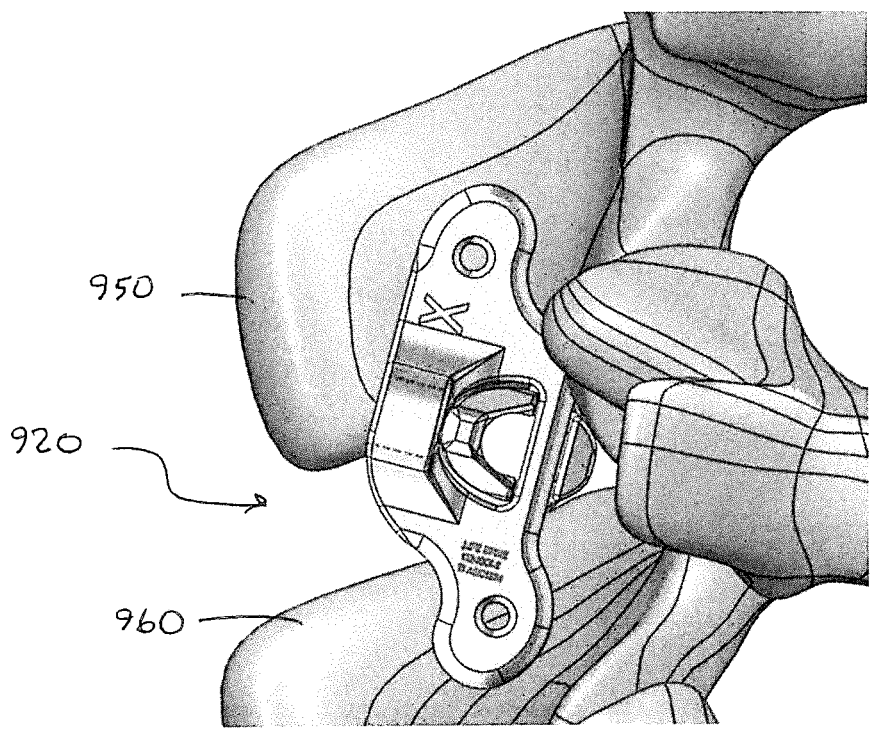
FIG. 37 is a side view of another implant in an implanted position according to another embodiment.

Referring now to FIGS. 36 and 37, implants (e.g., spinal implants) are shown according to various embodiments in implanted positions. For example, FIG. 36 shows an implant 910 positioned between a first bony structure 930 and a second bony structure 940 (e.g., vertebral bodies). As shown in FIG. 36, implant 910 may include a post having an aperture extending along the longitudinal axis of the post to facilitate placement of bone growth material. FIG. 37 shows an implant 920 positioned between a first bony structure 950 and a second bony structure 960 (e.g., vertebral bodies). Implants 910, 920 may include any or all of the features discussed with respect to the various implants and spacers disclosed herein.

The various spinal spacers are made from a biocompatible material such as PEEK, titanium or stainless steel. Other biocompatible materials or compounds may be used such as bone or an elastomeric or plastic other than PEEK. It should be appreciated that the present flexible spinal spacer may come in various sizes/dimensions to accommodate various spinal anatomies. Also, the body of the present spinal spacers may be other than H-shaped such as triangular or otherwise.

The spinal spacers of the figures are implanted between adjacent bony structures or protrusions (e.g. spinous process/transverse process) through an incision made in the patient proximate the area of implantation. Adjacent vertebrae are distracted and an appropriate spinal spacer is situated between the adjacent structures.

While the invention has been illustrated and described in detail in the drawings and foregoing description, the same is to be considered as illustrative and not restrictive in character, it being understood that only preferred embodiments have been shown and described and that all changes and/or modifications that come within the spirit of the present disclosure are desired to be protected.

What is claimed is:

1. A spinal spacer for insertion into a spinal space between a first vertebra and a second vertebra, the spinal spacer comprising:
    a body comprising:
        a first plate having a first wing configured to engage the first vertebra and a second wing configured to engage the second vertebra;
        a post extending from the first plate to define a longitudinal axis, the post having a bullet nose;
    a second plate slidably coupled to the post of the body, the second plate comprising:
        a first wing configured to engage the first vertebra; and
        a second wing configured to engage the second vertebra;
        wherein the second plate defines a first bore configured to receive the post;
    wherein the bullet nose is designed to pierce through an interspinous ligament between the first vertebra and the second the vertebra so that the interspinous ligament can hold the implant in place; and
    wherein the first wing and the second wing of the first plate each comprise a plurality of spikes extending toward the second plate.

2. The spinal spacer of claim 1, wherein the post further comprises an interior cavity and a second bore to provide access to the interior cavity.

3. The spinal spacer of claim 1, wherein the first bore in the second plate includes a planar portion and a curved portion to correspond with a planar portion and a curved portion on the post.

4. The spinal spacer of claim 3, wherein engagement of the planar and curved portions of the first bore on the second plate with the planar and curved portions on the post inhibit rotation of the second plate relative to the first plate.

5. The spinal spacer of claim 1, wherein the first wing and the second wing of the second plate each comprise a plurality of spikes extending toward the first plate.

6. The spinal spacer of claim 1, wherein the front portion of the second plate comprises a boss having a threaded third bore with an axis perpendicular to the longitudinal axis of the post.

7. The spinal spacer of claim 6, further comprising a screw received in the threaded third bore and configured to engage the post to secure the second plate relative to the body.

8. The spinal spacer of claim 1, wherein the first bore provides a continuous surface that surrounds at least a portion of the outer surface of the post.

9. A method of implanting a spinal spacer through an interspinous ligament and into a spinal space between a first vertebra and a second vertebra, the method comprising:
    providing a first plate, a post, and a second plate, the first plate having a first wing and a second wing, the post extending from the first plate to define a longitudinal axis, the post having a bullet nose, the second plate slidably coupled to the post and having a first wing, a second wing, and a bore to receive the post;
    pushing the bullet nose through the interspinous ligament;
    inserting the post in the spinal space between the first vertebra and the second vertebra; and
    inserting the second contoured plate onto the post.

10. The method of claim 9, wherein the step of inserting the second plate onto the post comprises aligning a planar portion and a curved portion of the bore on the second plate with a planar portion and a curved portion on the post.

11. The method of claim 9, further comprising sliding the second plate along the post so that the first wing and the second wing engage the first and second vertebra.

12. A spinal spacer for insertion into a spinal space between a first vertebra and a second vertebra, the spinal spacer comprising:
    a body comprising:
        a first plate having a first wing configured to engage the first vertebra and a second wing configured to engage the second vertebra;
        a post extending from the first plate along a longitudinal axis, the post having a bullet nose configured to pierce through an interspinous ligament between the first vertebra and the second the vertebra;
    a second plate slidably received on the post, the second plate comprising:
        a first wing configured to engage the first vertebra;
        a second wing configured to engage the second vertebra;
        a boss having a threaded first bore with an axis perpendicular to the longitudinal axis of the post;
        wherein the second plate defines a recess configured to receive the post,
        wherein positioning of the post within the recess inhibits rotation of the second plate relative to the first plate;
        a screw received in the threaded first bore in the boss and engaged with the post to secure the second plate relative to the first plate.

13. The spinal spacer of claim 12, wherein the post further comprises an interior cavity and a bore through the post to provide access to the interior cavity.

14. The spinal spacer of claim 12, wherein the first wing and the second wing of the first plate each comprise a plurality of spikes extending toward the second plate.

15. The spinal spacer of claim 12, wherein the first wing and the second wing of the second plate each comprise a plurality of spikes extending toward the first plate.

16. The spinal spacer of claim 12, wherein the recess provides a continuous surface that surrounds at least a portion of the outer surface of the post.

* * * * *